United States Patent
Reynolds

(10) Patent No.: US 11,717,536 B2
(45) Date of Patent: Aug. 8, 2023

(54) TREATMENT FOR PERIODONTITIS

(71) Applicant: THE UNIVERSITY OF MELBOURNE, Victoria (AU)

(72) Inventor: Eric Charles Reynolds, Victoria (AU)

(73) Assignee: THE UNIVERSITY OF MELBOURNE, Victoria (AU)

( * ) Notice: Subject to any disclaimer, the term of this patent is extended or adjusted under 35 U.S.C. 154(b) by 0 days.

(21) Appl. No.: 16/492,900

(22) PCT Filed: Mar. 14, 2018

(86) PCT No.: PCT/AU2018/050231
§ 371 (c)(1),
(2) Date: Sep. 10, 2019

(87) PCT Pub. No.: WO2018/165708
PCT Pub. Date: Sep. 20, 2018

(65) Prior Publication Data
US 2020/0054672 A1    Feb. 20, 2020

(30) Foreign Application Priority Data
Mar. 14, 2017   (AU) ................................ 2017900893

(51) Int. Cl.
*A61K 33/42*   (2006.01)
*A61K 9/68*    (2006.01)
*A61K 38/17*   (2006.01)

(52) U.S. Cl.
CPC ............ *A61K 33/42* (2013.01); *A61K 9/0058* (2013.01); *A61K 38/1709* (2013.01)

(58) Field of Classification Search
CPC ... A61K 33/42; A61K 9/0038; A61K 38/1709
See application file for complete search history.

(56) References Cited

U.S. PATENT DOCUMENTS

| | | |
|---|---|---|
| 3,864,471 A | 2/1975 | King et al. |
| 3,966,901 A | 6/1976 | Cullum et al. |
| 4,080,440 A | 3/1978 | Digiulio et al. |
| 4,157,386 A | 6/1979 | La Rochelle |
| 4,357,318 A | 11/1982 | Shah et al. |
| 4,522,805 A | 6/1985 | Gordan |
| 4,588,763 A | 5/1986 | Brannstrom et al. |
| 4,672,032 A | 6/1987 | Slavkin et al. |
| 5,015,628 A | 5/1991 | Reynolds et al. |
| 5,227,154 A | 7/1993 | Reynolds |
| 5,427,769 A | 6/1995 | Berrocal et al. |
| 5,520,725 A | 5/1996 | Kato et al. |
| 5,833,953 A | 11/1998 | Berrocal et al. |
| 5,981,475 A | 11/1999 | Reynolds |
| 6,036,944 A | 3/2000 | Winston et al. |
| 6,056,930 A | 5/2000 | Tung |
| 6,120,754 A | 9/2000 | Lee et al. |
| 6,149,894 A | 11/2000 | Yamane et al. |
| 6,214,101 B1 | 4/2001 | Nakaseko |
| 6,652,875 B1 | 11/2003 | Bannister |
| 6,780,844 B1* | 8/2004 | Reynolds ............... A61Q 11/00 514/5.5 |
| 7,312,193 B2 | 12/2007 | Reynolds et al. |
| 7,491,694 B2 | 2/2009 | Reynolds et al. |
| 8,354,117 B2 | 1/2013 | Tsunekawa et al. |
| 8,603,988 B2 | 12/2013 | Reynolds |
| 8,609,071 B2 | 12/2013 | Reynolds |
| 8,673,363 B2 | 3/2014 | Reynolds |
| 9,295,628 B2 | 3/2016 | Reynolds |
| 9,668,945 B2 | 6/2017 | Reynolds |
| 10,695,370 B2 | 6/2020 | Reynolds |
| 10,912,722 B2 | 2/2021 | Reynolds |
| 11,351,193 B2 | 6/2022 | Reynolds |
| 2002/0028251 A1 | 3/2002 | Okay |

(Continued)

FOREIGN PATENT DOCUMENTS

| | | |
|---|---|---|
| AU | 718253 | 7/1997 |
| CN | 103384526 A | 11/2013 |

(Continued)

OTHER PUBLICATIONS

Maria C. Martinez-Pabon, et al. Comparison of the effect of two sugar-substituted chewing gums on different caries- and gingivitis-related variables: a double-blind, randomized, controlled clinical trial. Clin Oral invest (2014) 18:589-598. (Year: 2014).*
Google scholar search_Sep. 21, 2020_GC Tooth Mousse periodontitis (Year: 2020).*
Google Search_Sep. 22, 2020_removing supragingival bacteria with brushing (Year: 2020).*
Google scholar search_Sep. 21, 2020_oral dysbiosis (Year: 2020).*
F.B. Zanatta. R.P. Antoniazzi. T.M.P. Pinto. C.K. Rösing. Supradindiva Daque Removal with and without. Dentifrice: A Randomized Controlled Clinical Trial. Braz. Dent. J. (2012) 23(3): 235-240. (Year: 2012).*
A.K. Sakr, A.A.M. ELkarargy, M.M. Sherif. The Effect of Recaldent (CPP-ACP) on the most putative bacteria in caries and chronic gingivitis. Ain Shams Dental Journal, vol. X, No. 2, Jun. 2007, 211-219. (Year: 2007).*
Google scholar search_Jun. 16, 2021_dysbiosis recaldent (Year: 2021).*

(Continued)

*Primary Examiner* — Michael P Cohen
(74) *Attorney, Agent, or Firm* — Foley & Lardner LLP

(57) ABSTRACT

The present invention relates to compositions and their use for oral care. In particular, the compositions and methods are for maintaining oral health and/or treating various oral conditions such as gingivitis. The present invention relates to methods and uses of stabilized amorphous calcium phosphate (ACP) and/or stabilized amorphous calcium fluoride phosphate (ACFP) in the preparation of a medicament for reducing pathogenic oral bacteria at an oral site in an individual; increasing commensal oral bacteria at an oral site in an individual; decreasing the proportion of pathogenic oral bacteria at an oral site in an individual; inhibiting oral dysbiosis; reducing gingival inflammation in an individual in need thereof; treating gingivitis in an individual in need thereof; and treating chronic gingivitis in an individual in need thereof.

12 Claims, 6 Drawing Sheets

(56) References Cited

U.S. PATENT DOCUMENTS

| | | |
|---|---|---|
| 2002/0071858 A1 | 6/2002 | Luo |
| 2003/0124066 A1 | 7/2003 | Dixon, Jr. et al. |
| 2003/0152525 A1 | 8/2003 | Dixon, Jr. et al. |
| 2003/0165442 A1 | 9/2003 | Baig et al. |
| 2005/0063922 A1 | 3/2005 | Reynolds et al. |
| 2005/0089481 A1 | 4/2005 | Yamanaka et al. |
| 2005/0100581 A1 | 5/2005 | Laurencin et al. |
| 2005/0118115 A1 | 6/2005 | Fontenot |
| 2006/0183081 A1 | 8/2006 | Bevilacqua et al. |
| 2007/0254260 A1 | 11/2007 | Alden, IV |
| 2008/0075675 A1 | 3/2008 | Reynolds |
| 2008/0171001 A1 | 7/2008 | Engelman et al. |
| 2008/0193557 A1 | 8/2008 | Reynolds et al. |
| 2009/0016972 A1 | 1/2009 | Manasherov et al. |
| 2009/0022672 A1 | 1/2009 | Reynolds |
| 2009/0324662 A1 | 12/2009 | Kutsch et al. |
| 2010/0028273 A1 | 2/2010 | Fischer et al. |
| 2011/0076241 A1 | 3/2011 | Kato et al. |
| 2012/0100194 A1* | 4/2012 | Yamai .............. A61K 8/735 424/48 |
| 2012/0129135 A1 | 5/2012 | Yang et al. |
| 2013/0129641 A1 | 5/2013 | Sadeghpour et al. |
| 2014/0147512 A1 | 5/2014 | Reynolds |
| 2016/0317404 A1 | 11/2016 | Reynolds |
| 2017/0333296 A1 | 11/2017 | Reynolds |
| 2018/0008518 A1 | 1/2018 | Reynolds |
| 2020/0197486 A1 | 6/2020 | Reynolds |
| 2020/0246378 A1 | 8/2020 | Reynolds |
| 2021/0161778 A1 | 6/2021 | Reynolds |
| 2022/0142881 A1 | 5/2022 | Reynolds |
| 2022/0183810 A1 | 6/2022 | Reynolds |

FOREIGN PATENT DOCUMENTS

| | | | |
|---|---|---|---|
| CN | 104921966 A | 9/2015 | |
| EA | 011125 B1 | 12/2008 | |
| EP | 0 786 245 A1 | 7/1997 | |
| EP | 1 525 878 A1 | 4/2005 | |
| EP | 1 525 878 B1 | 3/2007 | |
| EP | 2353576 A1 | 8/2011 | |
| JP | 8-143436 A | 6/1996 | |
| JP | 10-290682 A | 11/1998 | |
| JP | 11-310599 | 11/1999 | |
| JP | 3742523 | 11/1999 | |
| JP | 2001-144695 | 11/2002 | |
| JP | 2004-215521 A | 8/2004 | |
| JP | 2005-112841 | 4/2005 | |
| JP | 2005-145952 A | 6/2005 | |
| JP | 2010-047494 A | 3/2010 | |
| JP | 2013-163656 | 8/2013 | |
| WO | WO 1982/003008 | 9/1982 | |
| WO | WO 1987/007615 | 12/1987 | |
| WO | WO 1993/003707 | 3/1993 | |
| WO | WO 1994/00146 | 1/1994 | |
| WO | WO 1996/029340 | 9/1996 | |
| WO | WO 1997/036943 | 10/1997 | |
| WO | WO 1997/040811 | 11/1997 | |
| WO | WO 98/40406 | 9/1998 | |
| WO | WO 2000/006108 | 2/2000 | |
| WO | WO 2000/057842 A1 | 10/2000 | |
| WO | WO 2000/057892 | 10/2000 | |
| WO | WO 2001/044106 A1 | 6/2001 | |
| WO | WO-02/094204 A1 | 11/2002 | |
| WO | WO-03/059304 A1 | 7/2003 | |
| WO | WO 2003/059303 | 7/2003 | |
| WO | WO 2003/059303 A2 | 7/2003 | |
| WO | WO 2003/059304 A1 | 7/2003 | |
| WO | WO 2004/035077 A1 | 4/2004 | |
| WO | WO 2004/054531 A1 | 7/2004 | |
| WO | WO-2004/060336 A1 | 7/2004 | |
| WO | WO-2006/056013 A1 | 6/2006 | |
| WO | WO-2006056013 A1 * | 6/2006 | .............. C07K 7/06 |
| WO | WO-2006/130913 A1 | 12/2006 | |
| WO | WO-2006/135982 A1 | 12/2006 | |
| WO | WO-2007/090242 A1 | 8/2007 | |
| WO | WO-2009/099452 A1 | 8/2009 | |
| WO | WO 2009/130447 A1 | 10/2009 | |
| WO | WO-2010/134904 A1 | 11/2010 | |
| WO | WO-2012/100991 A1 | 8/2012 | |
| WO | WO-2013/117913 | 8/2013 | |
| WO | WO-2015/010166 A1 | 1/2015 | |
| WO | WO-2015/095932 A1 | 7/2015 | |
| WO | WO-2015095932 A1 * | 7/2015 | .............. A61K 33/42 |
| WO | WO-2018/165707 A1 | 9/2018 | |
| WO | WO-2018/165708 A1 | 9/2018 | |

OTHER PUBLICATIONS

Google scholar search_Jun. 16, 2021_ACP phosphopeptide and oral microbiome (Year: 2021).*

L.J. Walsh. "Clinical applications of Recaldent products: which ones to use where," Australasian Dental Practice May/Jun. 2007, 144-146. (Year: 2007).*

C. Llena, L. Forner, P. Baca. ("Anticariogenicity of Casein Phosphopeptide-amorphous Calcium Phosphate: A Review of the Literature," Journal of Contemporary Dental Practice, vol. 10, No. 3, May 1, 2009, 1-9). (Year: 2009).*

CPP-ACP_and_gingivitis_Google_Scholar_Dec. 13, 2021.pdf (Year: 2021).*

I. L. C. Chapple, et al. "Primary prevention of periodontitis: managing gingivitis," J Clin. Periodontol. 2015; 42 (Suppl. 16): S71-S76. (Year: 2015).*

L. Walsh. "Clinical Aspects of Salivary Biology for the Dental Clinician," International Dentistry South Africa (Australasian Edition) 9(4) (2007), 22-41 (Year: 2007).*

D. Munjal, et al.. "Assessment of White Spot Lesions and In-Vivo Evaluation of the Effectof CPP-ACP on White Spot Lesions in permanent Molars of Children," Journal of Clinical and Diagnostic Research, May 2016, vol. 10(5): 149-154. (Year: 2016).*

P.I. Eke, et al. "Prevalence of Periodontitis in Adults in the United States: 2009 and 2010." J Dent Res 91:914-920 (2012). (Year: 2012).*

Cai, "Effect of Addition of Citric Acid and Casein Phosphopeptide-Amorphous Calcium Phosphate to a Sugar-Free Chewing Gum on Enamel Remineralization in SITU," Caries Research (2007) vol. 41, pp. 377-383.

"Caseine phosphopeptide et phosphate de calcium amorphe: un complexe prometteur," Dialogue dentaire, Printemps 2005/W30, pp. 27-29. English Abstract provided.

"Colorimetry" Second Edition. By CIE Technical Committee. CIE 1986.

"Editors' Choice—Prospec MI Paste," The Dental Advisor, vol. 22, No. 5, Jun. 2005.

"GC Tooth Mousse—Eine ganz andere Art der Prävention," Dental Spiegel, Feb. 2005, pp. 53-54. English Abstract.

"Putting mouths where the money is.", DPRAsia, Jan./Feb. 2007, pp. 8-10.

"Tooth Mousse." Pierre qui roule n 'amasse pas mousse? Ben si! Clinic—Apr. 2006—vol. 27, p. 218-219, English Abstract provided.

"Tradition und moderns know how—ein Erfolgsrezept.", Zahn Prax8, vol. 5, 2005, p. 267. English Abstract.

Adamson et al., "Characteriztion of Tryptic Casein Phosphopeptides Prepared Under Industrially Relevant Conditions", Biotec. Bioeng., 45, pp. 196-204 (Feb. 1995).

Adamson et al., "High Performance Capillary Electrophoresis of Casein Phosphopeptides Containing 2-5 Phosphoseryl Residues; Relationship Between Absolute Electrophoretic Mobility and Peptide Charge and Size", Electrophoresis 16: pp. 525-528 (1995).

Adamson, et al., "Characterization of Casein Phosphopeptides Prepared Using Alcalase: Determination of Enzyme Specificity," *Enzyme and Microbial Tech.*, 19, pp. 202-207 (Aug. 1996).

Adamson, et al., "The Analysis of Multiple Phosphoseryl-containing Casein Peptides using Capillary Zone Electrophoresis," *J. of Chromatography*, 646, pp. 391-396 (Jun. 1993).

Adebayo, O.A. et al. "Effects of conditioners on microshear bond strength to enamel after carbamide peroxide bleaching and/or casein phosphopeptide-amorphous calcium phosphate (CPP-ACP) treatment", Journal of Dentistry, vol. 35, 2007, pp. 862-870 (Aug. 2007).

(56) References Cited

OTHER PUBLICATIONS

Akinmade et al., "Review Glass-Ionomer Cements as Adhesives, Part I, Fundamental Aspects and Their Clinical Relevance," Journal of Materials Science: Materials in Medicine, vol. 4, pp. 95-101 (1993).
Allais, G. "Karies—Die Therapie", Continuing Dental Education, pp. 716-735 (Jun. 2007), English Abstract provided.
Al-Zraikat, H. et al. "Development of GIC incorporating Caesin Phosphopetide amorphous phosphate (CPP ACP) complex.", Australian Dental Journal ADRF Special Research Supplement, vol. 52, p. S4., (2007).
Al-Zraikat, H. et al. "Incorporation of casein-phosphopeptide-amorphous calcium phosphate into glass ionomer cement." Abstract 0654—84th General Session of the IADR, Jun. 28-Jul. 1, 2006, Brisbane, Australia.
Angmar et al., "Studies on the Ultrastructure of Dental Enamel"; J. Ultrastructure Research, 8, pp. 12-23 (1963).
Aoba et al. "Dental Fluorosis: Chemistry and Biology."Crit. Rev Oral Biol. Med. 13 (2) pp. 155-170 (2002).
Ardu et al., "A minimally invasive treatment of severe dental fluorosis"; Quintessence International; 38(6), pp. 455-458 (Jun. 2007).
Ardu, S. et al. "Minimally invasive treatment of white spot enamel lesions.", Quintessenz International, vol. 38, No. 8, pp. 633-636 (Sep. 2007).
Aytepe, Z. et al. "Effect of CCP-ACP on oral health of cerebral palsy children.", Abstract 3343, Jul. 2008, International Association for Dental Research, Toronto, Canada.
Baig, et al., "HAP Dissolution Study II: $SnF_2$ vs. NaF Dentifrice Study," 87th Session of the IADR (International & American Associations for Dental Research) Apr. 1-4, 2009 [on line], [retrieved on Oct. 21, 2014], Retrieved from internet ,URL: dentalcare.com/media/en-US/research_ db/pdf/, p. 24.
Bavetta et al., "Protein Factors and Experimental Rat Caries", Journal of Nutr. 63: pp. 107-117 (1957).
Benzian et al., "Total and free available fluoride in toothpastes in Brunei, Cambodia, Laos, the Netherlands and Suriname"; International Dental Journal, 62, pp. 213-221 (2012).
Biesbrock, A.R. et al. "Reversal of Incipient and Radiographic Caries Through The Use of Sodium and Stannous Fluoride Dentifrices in a Clinical Trial." The Journal of Clinical Dentistry vol. IX, No. 1, pp. 5-10 (Feb. 1998).
Biesbrock, Aaron R. "Relative anti-caries efficacy of 1100, 1700, 2200, and 2800 ppm fluoride ion in a sodium fluoride dentifrice over 1 year." Community Dentistry and Oral Epidemiology; 29, pp. 382-389 (Jan. 2001).
Biesbrock, Aaron R. et al. "Dose response efficacy of sodium fluoride dentrifice at 9 and 21 months with supervised brushing." American Journal of Dentistry, vol. 16, No. 5, 9. 305-312 (Oct. 2003).
Black et al. "Mottled Teeth" The Dental Cosmos. vol. LVIII. No. 2., pp. 129-156 (Feb. 1916).
Burwell, A.K. et al. "Dentifrice Protection Against Dentin Demineralization in an In Vitro Study.", Abstract 1764, IADR, New Orleans, USA (Mar. 2007).
Burwell, A.K. et al. "Quantitative Tubule Occlusion in an In Vitro Remineralization/Demineralization Model.", Abstract 0568, EADR 2006, Dublin, Ireland (Sep. 2006).
Cai et al., "Remineralization of Enamel Subsurface Lesions in Situ by Sugar-Free Lozenges Containing Casein Phosphopeptide-Amorphous Calcium Phosphate", Aus. Dent. J., 48: 4, pp. 240-243 (2003).
Cai, F. et al. "Effect of Addition of Citric Acid and Casein Phosphopeptide-Amorphous Calcium Phosphate to a Sugar-free chewing gum on Enamel Remineralization in Situ.", Caries Research, vol. 41, pp. 377-383 (Feb. 2007).
Cai, F. et al. "Remineralization by chewing gum containing CPP-ACP and citric acid." Abstract 190-84th General Session of the IADR, Brisbane, Australia, pp. 240-243 (Jun. 28, 2006-Jul. 1, 2006).

Calcium Glycerophosphate, DrugBank, pp. 1-5, XP002783472 (created Mar. 12, 2015) (retrieved Jul. 31, 2018).
CAPLUS Copyright 2005. "NMR studies of a novel Calcium, phosphate and fluoride delivery vehicle <SYM97> S1-casein( 59-79) by stabilized amorphous calcium fluoride phosphate nanocomplexes."
Carrillo, Dr. J et al. "Nuevos avances tecnologicos en Odontologia Conservadora", La Gaceta Dental, 193:213, pp. 218-219 (Jun. 2008), English Abstract.
Chalmers, J. et al. "Minimal Intervention Dentistry in the New Millennium," Dentaltown, pp. 54 (Feb. 2008).
Chalmers, J.M. "Minimal intervention dentistry: part 1. Strategies for addressing the new caries challenge in older patients." JCDA, 72(5), pp. 427-433 (Jun. 2006).
Chelariu, C. et al. "Nuove prospettive nella prevenzione della carle Congresso Nazionale del Collegio dei Docenti di Odontoiatria Roma", Apr. 5-7, 2006, Poster session, published by "Doctor Os", No. 3, Mar. 2006. English Abstract.
Chen, L. et al. "Calcium Release and Mechanical Properties of Experimental Calcium-Releasing Composites.", Abstract 2572, IADR, New Orleans, USA (Mar. 2007).
Cipolla, M. et al. "Fluoride and Calcium-Phosphate Effects on Fracture Toughness of Bleached Dentin.", Abstract 1032, Toronto, Canada (Jul. 2008).
Coates, L. "Tooth mousse shows some unexpected beneficial side effects." Dental Asia (Nov./Dec. 2004), pp. 40-43.
Cochrane, N.J. et al. "QLF and TMR analysis of CPP-ACFP remineralized enamel in vitro.," Abstract 192—84th General Session of the IADR, Brisbane, Australia (Jun. 28, 2006-Jul. 1, 2006).
Comar et al., "Effect of NaF, $SnF_2$, and$TiF_4$ Toothpastes on Bovine Enamel and Dentin Erosion-Abrasion In Vitro," International Journal of Dentistry, vol. 2012, Article IDS 134350, pp. 1-6 (Oct. 2012).
Crisp, S., "Glass Ionomer Cement: Chemistry of Erosion", J. Dent. Res. 55: 1032-1041 (Apr. 1976).
Cross et al. "Casein Phosphopeptide-Amorphous Calcium Phosphate Nanocomplexes: A Model of the Casini Micelle Core," Centre for Oral Health Science, School of Dental Science, The University of Melbourne, pp. 1-42, (Aug. 2008).
Cross et al., "Cation-Dependent Structural Features of Beta-Casein-(1-25)", Biochem. J. (May 15, 2001), 356: Pt 1, pp. 277-286.
Cross et al., "NMR Studies of a Novel Calcium, Phosphate and Fluoride Delivery Vehicle—The Multiphosphorylated Peptide Alpha S1-Casein (59-79) Complexed with Amorphous Calcium Fluoride Phosphate", Biomaterials., vol. 25, pp. 5061-5069 (Jan. 2004).
Cross et al., "Structural Studies of the b-Casein Phosphopeptide Bound to Amorphous Calcium Phosphate", IADR, General Session, J. Dent. Res. Vo. 80, p. 588 Chiba, Abstract 0490, (2001). (IADR Abstracts).
Cross et al., "Ultrastructural Studies of the Casein Phosphopeptide-Amorphous Calcium Phosphate Nanoclusters", IADR, General Session, J. Dent. Res. Vo. 80, p. 588, Chiba, Abstract 0491, (2001). (IADR Abstracts).
Cross, et al. "Physicochemical Characterization of Casein Phosphopeptide-Amorphous Calcium Phosphate Nanocomplexes." The Journal of Biological Chemistry, vol. 280, No. 16. 15362-15369 (Apr. 2005).
Cross, K.J. et al. Structure and $^{15}$N-Dynamics of casein phosphopeptide-amorphous calcium phosphate nanocomplexes. Abstract 2534—84th General Session of the IADR, Jun. 28-Jul. 1, 2006, Brisbane, Australia.
Cross, KJ et al. "Casein Phosphopeptides in Oral Health—Chemistry and Clinical Applications", Current Pharmaceutical Design, vol. 13, pp. 793-800 (2007).
Cross, KJ et al. "Structural Characterization of anticariogenic casein Phosphopeptide alphas2 casein(46-70) complexed with amorphous calcium phosphate.", Aust Dent J ADRF Special Research Supplement 52(4):S10-S11 (2007).
Cross, KJ et al. "Structural Characterization of Beta-casein(1-25)-ACFP Complex.", Aust Dent J ADRF Special Research Supplement, vol. 52, No. 4, S12, (2007).
Curnow, M.M.T., et al. "A Randomised Controlled Trial of the Efficacy of Supervised Toothbrushing in High-Caries-Risk Children." Carie Research; 36:294-300 (Mar. 2002).

(56) References Cited

OTHER PUBLICATIONS

Database WPI Week 200316, Thomason Scientific, London, GB; 2003-165149, XP002537968 & SE 0 100 558 A, Mediteam Dental AB, Aug. 21, 2002, Abstract.
Davies, G.M., "A randomized controlled trial of the effectiveness of providing free fluoride toothpaste from the age of 12 months on reducing caries in 5-6 year old children." Community Dental Health 19, 131-136 (2002).
Deangelis et al., "Molecular modelling of anticariogenic Casein Phosphopeptide AS2-CN (2-20) NMR Spectroscopy Derived Constraints", Abstract 2997—82$^{nd}$ General Session of the IADR, Mar. 2004, Honolulu, Hawaii.
Denbesten, P.K. et al. "Biological Mechanisms of Fluorosis and Level and Timing of Systemic Exposure to Fluoride with Respect to Fluorosis." J. Dent Re 71(5): pp. 1238-1243 (May 1992).
Donovan, T. "Protocol for the prevention and management of root caries.", Journal Compilation, vol. 20, No. 6, pp. 405-411 (2008).
Duckworth, R.M. "Effects of Mouthwashes of Variable NaF Concentration but Constant NaF Content on Oral Fluoride Retention." Caries Research 1994; 28, pp. 43-47 (1994).
Duckworth, R.M. "Oral Fluoride Measurements for Estimation of the Anti-caries Efficacy of Fluoride Treatments." J Dent Res., vol. 71, pp. 836-840 (Apr. 1992).
Fahad, et al., "Effect of casein phosphopeptide-amorphous calcium phosphate on the microhardness and microscopic features of the sound enamel and initial caries-like lesion of permanent teeth, compared to fluoridated agents," Journal of Baghdad College Dentistry, vol. 24, No. 4, pp. 114-120 (2012).
Featherstone, Job et al. "An in situ model for simultaneous assessment of inhibition of demineralization and enhancement of Remineralization." J Dent Res vol. 71 (Spec. Iss.), pp. 804-810 (Apr. 1992).
Feinmann, J. "This won't hurt a bit," The Times, Saturday, 2 pages, Mar. 12, 2005.
Fejerskov et al. "Dental fluorosis—a handbook for health workers." Munksgaard, Copenhagen, pp. 32-77 (copyright 1988).
Fejerskov et al. "Fluoride in Dentistry $2^{nd}$ edition." Munksgaard, Copenhagen, pp. 112-152 (Copyright 1996).
Fejerskov et al. "Posteruptive changes in human dental fluorosis—a histological and ultrastructural study." Pro Finn Dent Soc vol. 87, No. 4, pp. 607-619 (1991).
Fejerskov et al. "The Nature of Mechanisms of Dental Fluorosis in Man." J Dent Res 69 (Spec Iss) pp. 692-700 (Feb. 1990).
Ferrazzano, G. et al. "Protective effect of yogurt extract on dental enamel demineralization in vitro," Australian Dental Journal, vol. 53, pp. 314-319 (Feb. 2008).
Ferrazzano, G.F. et al. "New Strategies in dental caries prevention: experimental study on casein phosphopetide.", European Journal of Paedetric Dentistry, 4, pp. 183-187 (Apr. 2007).
Ferrazzano, G.F. et al. "Nuove strategie nella prevenzione della carle dentaria:studio sperimentale sui caseinofosfopeptidi." Prevenzione Odontostomatologica vol. 4, 2005, pp. 15-21. English Abstract.
Freml, L. et al. "Efficacy of Hypersensitivity Agents on Demineralization under Provisional Crowns." Abstract 1346, IADR Mar. 2007, New Orleans, USA.
Fuller, B.L. et al. "Efficacy of Ml Paste in Preventing Demineralization in Overdenture Abutments," Abstract 0503, IADR Mar. 2007, New Orleans, USA.
Gagnaire et al., "Phosphopeptides interacting with colloidal calcium phosphate isolated by tryptic hydrolysis of bovine casein micelles", Journal of Dairy Research (Feb. 1996), 63, pp. 405-422.
Gandolfi, M. et al. "Calcium silicate coating derived from Portland cement as treatment for hypersensitive dentine", Journal of Dentistry, vol. 36, 2008, pp. 565-578.
GC America, Inc. "MI Paste™ and MI Paste Plus™ with RECALDENT™ (CPP-ACP)" Inside Dentistry, Oct. 2012, vol. 8, No. 10 [online], [retrieved on Oct. 21, 2014], Retrieved from internet, URL: www .dentalaegis.com/id/201 21 1 O/mi-paste-and-mi-paste-p l us-with-recaldent-cpp-acp>, 6 pages.

GC stellt Kasein-haltige Zahnschutzcreme vor—Vorbeugen start reparieren DZW Special IDS-Nachlese. 2005. English Abstract, pp. 10-11.
Giambro, N.J. et al. "Characterization of Fluorosed Human Enamel by Color Reflectance, Ultrastructure, and Elemental Composition." Caries Res. Issue 29 (Jan. 1995) pp. 251-257.
Giniger et al. "A 180-Day Clinical Investigation of the Tooth Whitening Efficacy of a bleaching Gel with Added Amorphous Calcium Phosphate." J. of Clinical Dentistry. vol. XVI. No. 1. 2005. pp. 11-16.
Giniger et al. "The clinical performance of professionally dispensed bleaching gel with added amorphous calcium phosphate." JADA. vol. 136. Mar. 2005. pp. 383-392.
Gisselsson, H., et al. "Effect of professional flossing with NaF or $SnF_2$ gel on approximal caries in 13-16-year-old schoolchildren". Acta Odontologica Scandinavica, vol. 57, No. 2, pp. 121-125 (Jan. 1999).
Gugnani, S. et al. "Comparative evaluation of two commercially available 8odems8te8pha agents after scaling and root planning: an in vivo study", PERIO, vol. 5, No. 2, 2008, pp. 121-129.
Haderlie, D.D. et al. "MI Paste and Fluoride effects on Secondary Caries.", Abstract 0504, IADR Mar. 2007, New Orleans, USA.
Harper et al., "Cariostatic Evaluation of Cheeses with Diverse Physical and Compositional Characteristics", Caries Res. 20: pp. 123-130 (1986).
Harper et al., "Modification of Food Cariogenicity in Rats by Mineral-Rich Concentrates from Milk", J. Dent Res. 66: pp. 42-45 (Jan. 1987).
Hartshone, JE. "The relationship between plaque index scores, fluoride content of plaque, plaque pH, dental caries experience and fluoride concentration in drinking water in a group of primary school children." Journal of the Dental Association of South Africa, 49, pp. 5-10, Jan. 1994.
Hay et al., "A Clinical Trial of the Anticaries Efficacy of Casein Derivatives Complexed with Calcium Phosphate in Patients with Salivary Gland Dysfunction", Oral. Surg. Oral Med Oral. Pathol Oral Radiol. Endod. (Mar. 2002); 93: pp. 271-275, 2002.
Hicks, J. et al. "Biological factors in dental caries: role of remineralization and fluoride in the dynamic process of demineralization and remineralization (part 3)." The Journal of Clinical Pediatric Dentistry. vol. 28, No. 3, pp. 203-214 (2004).
Hicks, J. et al. "Casein Phosphopeptide-Amorphous calcium phosphate paste: root surface caries formation," Abstract 3275—IADR, Mar. 2005, Baltimore, Maryland, USA, Abstract.
Hidaka, et al., "A New Method for Study of the Formation and Transformation of Calcium Phosphate Precipitates: Effects of Several Chemical Agents and Chinese Folk Medicines," *Archives of Oral Biol.*, 36:1, pp. 49-54 (1991).
Holler, B. E. et al. "Fluoride uptake and distribution in enamel and dentin after application of different fluoride solutions." Clin Oral Invest, vol. 6, 2002, pp. 137-144.
Holloway et al., "Effects of Various Sucrose-Casein Ratios in Purified Diets on the Teeth and Supporting Structures of Rats", Arch Oral Biol. 3: pp. 185-200 (1961).
Holt, Carl. "An equilibrium thermodynamic model of the sequestration of calcium phosphate by casein micelles and its application to the calculation creme partition of salts in milk." European Biophysics Journal. (Jan. 2004) pp. 421-434.
Holt, et al., "Ability of a b-casein Pho/sphopeptide to Modulate the Precipitation of Calcium Phosphate by Forming Amorphous Dicalcium Phosphate Nanoclusters," *Biochem J.*, 314, 1035-1039 (1996).
Huang, A. et al. "Remineralization of eroded teeth using CPP-ACP paste," Abstract 3267, Jul. 2008, International Association for Dental Research, Toronto, Canada.
Huq et al., "Molecular Modeling of the Multiphosphorylated Sequence Motif Bound to Hydroxyapatite Surfaces" (59-79), J. Mol. Mode (Feb. 2000), 6:35-47.
Huq et al., "Molecular Modelling of the Multiphosphorylated Casein Phosphopeptide Alpha S1-Casein (59-79) based on NMR constraints," J. Dairy Res. 71:28-32 (2004).
Huq, et al. "Nascent Helix in the Multiphosphorylated Peptide $a_{s2}$-Casein(2-20)." Journal of Peptide Science, (2003) pp. 386-392.

(56) References Cited

OTHER PUBLICATIONS

Huq, et al., A H-NMR Study of the Casein Phosphopeptide $a_{s1}$ Casein (59-79) Biochimica et Biophysica Acta, 1247, 201-208 (1995).
Iijima et al., "Acid Resistance of Enamel Subsurface Lesions Remineralized by a Sugar-Free Chewing Gum Containing Casein Phosphopeptide-Amorphous Calcium Phosphate (CPP-ACP)", Caries, Res. Jan. 2004; 38: pp. 551-556.
Iijima, Y. et al. "Acid resistance of remineralized enamel by a sugar-free chewing gum.", Abstract 184—$84^{th}$ General Session of the IADR, Jun. 28-Jul. 1, 2006, Brisbane, Australia.
Imfeld, "Prevention of progression of dental erosion by professional and individual prophylactiv measures," Eur J Oral Sci (1996) 104:215-220.
Inaba, D et al. "Effect of Sodium Hypochlorite Treatment on Remineralization of Human Root Dentine in vitro." Caries Research 1996, vol. 30 pp. 218-224.
Inaba, D. et al. "Intraoral changes in NaOCl-treated Root Dentin Lesions: A Pilot Study.", J. Dental Health, vol. 50, Jul. 2000, pp. 824-826. Abstract.
International Search Report dated Sep. 25, 2016 in application No. PCT/AU2006/000885.
International Search Report dated Sep. 15, 2014 in application No. PCT/AU2014/050144.
Japanese Examination Report for corresponding Japanese Patent Application No. 2008-515000 dated Mar. 7, 2013. English Translation.
Kandelman, D et al. "A 24-month clinical study of the incidence and progression of dental caries in relation to consumption of chewing gum containing xylitol in school preventive programs." J Dent Res vol. 69(11), Nov. 1990, pp. 1771-1775.
Kariya et al., "Fluoride Effect on Acid Resistance Capacity of CPP-ACP Containing Material", Abstract 2045—$82^{nd}$ General Session of the IADR, (Mar. 2004), Honolulu, Hawaii. Abstract.
Kariya, S. et al. "Remineralization of enamel lesion by a novel cream with both CPP-ACP and fluoride," Poster session 136—$54^{th}$ Annual ORCA Congress, 2007. Abstract.
Keçik, D. et al. "Effect of Acidulated Phosphate Fluoride and Casein Phosphopeptide-Amorphous Calcium Phosphate Application on Shear Bond Strength of Orthodontic Brackets." Angle Orthodontist, vol. 78, No. 1, 2008, pp. 129-133.
Khan, Dr. S. "White Spots on Teeth", Buzzle.com Intelligent Life on the Web, Jan. 2010.
Kim, K. et al. "Remineralization of the artificial caries lesion using CPP-ACP and fluoride.", Abstract 3280, Jul. 2008, International Association for Dental Research, Toronto, Canada.
Kowalczyk et al. "Evaluation of the product based on Recaldent™ technology in the treatment of dentin hypersensitivity.", Advances in Medical Sciences, vol. 51 suppl 1, 40-42, Mar. 2006.
Krobicka et al., "The Effects of Cheese Snacks on Caries in Desalivated Rats", J. Dent Res. 66:1116-19, (Jan. 1987).
Kumar, Vln et al. "The effect of casein phosphopeptide-amorphous calcium phosphate on remineralization of artificial caries-like lesions: an in vitro study.", Australian Dental Journal, vol. 53, 2008, pp. 34-40.
Larsson, K. S., et al. "Fluoride concentration in plaque in adolescents after topical application of different fluoride varnishes." Clin Oral Invest. (2000) 4:31-34.
Lasfargues, J. et al. "La remineralisation des lesions carieuses (2) synergies therapautiques Realites Cliniques.", vol. 15, No. 3, 2004 pp. 261-275. English Abstract.
Legeros, RZ "Calcium phosphates in demineralization/remineralization processes." J Clinical DentX, 1999, pp. 65-73.
Lewis, J. "Brush, floss and mousse?" Women Dentistry Journal, Winter 2005, vol. 2, Issue 4, 18-19.
Little, Elaine et al. "An equilibrium thermodynamic model of the sequestration of calcium phosphate by casein phosphopeptides." European Biophysics Journal. (Jan. 2004) 33, 435-447.
Loesche, WJ "Role of Streptococcus mutans in human dental decay." Microbial. Rev. vol. 50(4), Dec. 1950, pp. 353-380.

Lynch, R.J.M. et al., "Low-Levels of Fluoride in plaque and saliva and their effect on the demineralization and remineralisation of enamel; role offluoride of toothpastes." International Dental Journal (2004) vol. 54/ No. 5, 304-309.
Malcmacher, L. "Enamel Remineralization: The Medical Model of Practicing Dentistry.", Dentistry Today, Nov. 2006, 4 pages.
Malcmacher, L. "Vitamins for teeth.", Common Sense Dentistry, Dental economics Oct. 2006, 130 and 144.
Manton, D. "Dental Caries: Where to From Here?", Ann Roy Austral Coll Dent Surg, vol. 19, 2008, pp. 73-76.
Manton, D. et al. "Effect of ozone and Tooth Mousse™ on the efficacy of peroxide bleaching," Australian Dental Journal, vol. 53, 2008, pp. 128-132.
Manton, D. et al. "Remineralization of enamel subsurface lesions in situ by the use of three commercially available sugar-free gums.", International Journal of Paediatric Dentistry, vol. 18, 2008, pp. 284-290.
Manton, D. J. et al. "Remineralization of white spot lesions in situ by tooth mousse." Abstract 185—$84^{th}$ General Session of the IADR, Jun. 28-Jul. 1, 2006, Brisbane, Australia, Abstract.
Manton, D.J. "Promoting remineralization: using casein phosphopeptide-stabilized amorphous calcium (fluoride) phosphate. A chemical approach." EAPD, Amsterdam 8-II Jun. 2006, Abstract.
Manton, D.J. et al. "In situ remineralisation by sugar-free gums, one containing CPP-ACP." Abstract 0020—$45^{th}$ Annual Meeting of Australian/New Zealand Division of the IADR, Sep. 2005, pp. 25-28.
Ma77aoui, S.A. et al. "Incorporation of Casein Phosphopeptide-Amorphous Calcium Phosphate into a Glassionomer Cement." School of Dental Science, The University of Melbourne Research Reports (Jul. 2003) pp. 914-918.
Melkers, M.J. "Keeping focused on the finish line. Accomplishing goals with traditional and progressive technologies," Dentaltown, vol. 5—Issue 11, Nov. 2004, pp. 60, 62, 64 & 66.
Mellberg, J.R. et al. "Effect of soluble calcium on fluoride uptake by enamel from sodium monofluorophosphate" J Dent Res. 1982 vol. 61, No. 12, pp. 1394-1396.
MI Paste™ and MI Paste Plus™ [retrieved on Feb. 16, 2015] Retrieved from internet ,URL: http://web.archive.org/web/20140701070616/http://www.mipaste.com/about.php> published on Dec. 4, 2013 as per Wayback Machine whole document Wayback machine used to determine publication date, 2 pages.
MI Paste™ and MI Paste Plus™ [retrieved on Oct. 21, 2014] Retrieved from internet, URL: http://web.archive.org/web/20331223044I14/http://www.gcamerica.com/products/preventive/MI _Paste/> published on Dec. 23, 2013 as per Wayback Machine whole document Wayback machine used to determine publication date, 2 pages.
Mickenautsch, S. "An Introduction to Minimal Intervention Dentistry (MI).", Dental News, vol. XIV, No. IV, 2007, pp. 13-20.
Milnar, F.J. "Considering biomodification and remineralization techniques as adjuncts to vital tooth-bleaching regimens," Compendium vol. 28, No. 5, May 2007, pp. 234-240.
Minami et al., "Effects of Cheese and Milk Containing CPP-ACP on Enamel Remineralization", 2049—$82^{nd}$ General Session of the IADR, Mar. 2004, Honolulu, Hawaii. Abstract only.
Minimale Intervention für maximale Mundgesundheit, DZW Special. Mar. 2005. English Abstract.
Minimum Intervention: modernes Kariesmanagement—Weg vom chirurgichen, hin zum medizinischen Versorgungsansatz mit GC. IDS—$31^{st}$ International Dental Show, Cologne, Apr. 12-16, 2005 (Today—Independent Trade Show Daily—Saturday) English Abstract.
Mintel, "Mineralising Toothpaste," from Database GNPD, database accession No. 1368327 (Aug. 2010).
Misra, S. et al. "Early Childhood Caries—A Review," Dental Update, vol. 34, Dec. 2007, pp. 556-564. Abstract.
Miyazaki, M. et al. "Using ultrasound transmission velocity to analyze demineralization of tooth substrate." Abstract 94—$52^{nd}$ ORCA Congress, Jul. 2005, Indianapolis, USA I Caries Res vol. 39:319.
Morgan, M. V. et al. CPP-ACP gum slows progression and enhances regression of dental caries. Abstract 2445—$84^{th}$ General Session of the IADR, Jun. 28-Jul. 1, 2006, Brisbane, Australia. Abstract.

(56) References Cited

OTHER PUBLICATIONS

Morgan, MV et al. "A Clinical Trial Measuring White Spot Lesion Progression and Regression," Abstract 0112, Jul. 2008, Toronto, Canada.
Morgan, MV et al. "Clinical trial of tooth mousse on white spot lesions.", Cooperative research Centre for oral health science. Toronto, Briefing paper No. 2, 2008.
Morgan, MV et al. "The Anticariogenic Effect of Sugar-Free Gum Containing CPP-ACP Nanocomplexes on Approximal Caries Determined Using Digital Bitewing Radiography.", Caries Research, vol. 42, pp. 171-184, 2008.
Moule, C.A et al. "Resin bonding using an all-etch or self-etch adhesive to enamel after carbamide peroxide and/or CPP-ACP treatment," Australian Dental Journal, vol. 52, No. 2, 2007, pp. 133-137.
Mount, GJ, "A new paradigm for operative dentistry,", Australian Dental Journal vol. 52, No. 4, 2007, pp. 264-270.
Murata et al., "Remineralization Power by Xylitol Chewing Gums", Abstract 2046—$82^{nd}$ General Session of the IADR, 2004, Honolulu, Hawaii. Abstract only.
Narayana, T. et al. "An in vitro study of wear prevention in dentine." Abstract 2424—$84^{th}$ General Session of the IADR, Jun. 28-Jul. 1, 2006, Brisbane, Australia.
Ng, H. et al. "Aesthetic management of severely fluorosed incisors in an adolescent female." Australian Dental Journal, vol. 52, No. 3, 2007, pp. 243-248.
O'Hehir, T "Caries—More than a filling," Hygientown.com, Jul./Aug. 2008, pp. 8-12.
Ono et al., "Complexes of Casein Phosphopeptide and Calcium Phosphate Prepared from Casein Micelles by Tryptic Digestion", Biosci. Biotech. Biochem. 58 (8), pp. 1376-1380, 1994.
Ono et al., "Preparation of Casein Phosphopeptides from Casein Micelles by Ultrafiltration", Biosci. Biotech. Biochem. 59 (3), pp. 510-511, 1995.
Oshiro, M. et al. "Effect of CPP-ACP paste on tooth mineralization: an FE-SEM study." Journal of oral Science, vol. 49, No. 2, 2007, pp. 115-120.
Pelletier et al. "Etude de la Réaction d'Hydrolyse de l'Anion P03F2- en Solution Aquese" Z. anorg. Allg. Chem. 581 (1990) 190-198.
Perdigao, J. et al. "Contemporary Trends and Techniques in Tooth Whitening: A Review", Practical Procedures & Aesthetic Dentistry, vo. 16, No. 3, 2004, pp. 185-192.
Perich et al., "Efficient Solution-Phase Synthesis of Multiple O-Phosphoseryl-Containing Peptides Related to Casein and Statherin", Int. J. Pept. Protein Res. (Aug. 1992), 40:2 pp. 81-88.
Perich et al., "The Use of Synthetic Phosphopeptides for Epitope Mapping of the ASI-Casein Phosphopeptide Segment 59-70", Bioorg. Med. Chem. Lett. (1992), 2: pp. 1153-1154.
Peschke, J.C. et al. "Nucleating Ability of Calcium Phosphate-Protein-Composites.", Abstract 2244, IADR Mar. 2007, New Orleans, USA.
Piekarz, C. et al. "An in vitro assessment of the role of Tooth Mousse in preventing wine erosion.", Australian Dental Journal, vol. 53, 2008, pp. 22-25.
Pietrzycka, K. "Chemical methods of treatment of dental caries: the action and application of CPP-ACP.", E-Dentico, vol. 2, No. 18, 2008, pp. 68-74. English Abstract.
Pitts, N.B. "Are we ready to move from operative to non-operative/preventive treatment of dental caries in clinical pmctice?", Caries Res, vol. 38, 2004, pp. 294-304.
Plate, U. et al. Investigation of the early mineralization on collagen in dentine of rat incisors by quantitative electron spectroscopic diffraction (ESD), Cell Tissue Res, vol. 278, 1994, pp. 543-547.
Poitevin et al., "Clinical Effectiveness of a CPP-ACP Crème for Tooth Hypersensitivity Treatment", EADR Istanbul, (Aug. 24-28, 2004), Abstract 0136.
Preventive agents; The Dental Advisor; 21(10):1-6 (Dec. 2004).
Products for the dental hygienist—Desensitizers. The Dental Advisor, vol. 23, No. 6, Jul./Aug. 2006.

Quartarone, E. "Surface kinetic roughening caused by dental erosion: an atomic force microscopy study.", Journal of Applied physics, vol. 103, 2008, 104702, 1-6.
Rahiotis, C. et al. "Characterization of oral films formed in the presence of a CPP-ACP agent: An in situ study.", Journal of dentistry, vol. 36, 2008, pp. 272-280.
Rahiotis, C. et al. "Effect of a CPP-ACP agent on the demineralization and remineralization of dentine in vitro.", Journal of Dentistry, vol. 35, 2007, pp. 695-698.
Ramadas, "The oral care for children with malignancies"; Synopses; Synopses: The Newsletter of the Australian and New Zealand Society of Paediatric Dentistry, Winning 2003 Postgraduate Essay; 28:1-20 (Mar. 2004).
Ramalingam et al., "An in Vitro Investigation of the Effects of Casein Phosphopeptide-Stabilized Amorphous Calcium Phosphate (CPP-ACP) on Erosion of Human Dental Enamel by a Sports Drink", IADR, General Session, San Diego (2002), Abstract 2810.
Ramalingam et al., "Erosion of Human Dental Enamel by Sports Drinks", Synopses 27:16-19, (2003).
Ramalingam, L. et al. "Adding Caesin Phosphopetide-amorphous Calcium Phosphate to Sports Drinks to Eliminate In Vitro Erosion.", Pediatric Dentistry, vol. 27, No. 1, 61-67, 2005.
Ranjitkar, S. et al. Enamel wear prevention under conditions simulating bruxism and acid regurgitation. Abstract 2428—$84^{th}$ General Session of the IADR, Jun. 28-Jul. 1, 2006, Brisbane, Australia.
Ranjitkar, S. et al. "The Role of Tooth Mousse in preventing enamel wear," Poster 0375—session 39—$42^{nd}$ annual meeting of IADR-Continental European and Israeli Divisions, Sep. 26-29, 2007.
Ranjitkar, S. et al. "The role of tooth mousse in reducing erosive tooth wear," Abstract 2500, Jul. 2008, International Association for Dental Research, Toronto, Canada.
Rees, J. et al. "Pronamel and tooth mousse: An initial assessment of erosion prevention in vitro.", Journal of Dentistry, vol. 35, 2007, pp. 355-357.
Reeves et al., "Calcium Phosphate Sequestering Phosphopeptide from Casein." Science. vol. 128, p. 472 (1958).
Reich, E. "Das kleine gewisse Etwas zur Remineralisation", Zahnmedizin, vol. 95, No. 21, 2-9, 2005. English Abstract.
Reich, E. "Die Betreuung von Kariespatienten in der Praxis", Quintessenz, vol. 59, No. 12, 2008, pp. 1301-1307. English Abstract.
Reich, E. "Flüssiger Zahnschmelz." Dental Magazine. 2005. English Abstract.
Reich, E. "GC Tooth Mousse—Ein neuer Ansatz zur Remineralisation", Kongress: Wissenschaft und Praxis der Sanften Zahnheilkunde, Lindau am Bodensee, Mar. 3-4, 2006. English Abstract.
Reich, E. Dental Products Report Europe, Jan. 1, 2006.
Reynolds et al. "Additional Aids to the Reminersalisation of Tooth Structure," Preservation and Restoration of Tooth Structure Chapter 8, 111-118, 2005.
Reynolds et al., (1982) Phosphoprotein inhibition of Hydroxypatite dissolution. Calcif. Tissue Int. 34: S52-S56.
Reynolds et al., (1983) Effect of adsorbed protein on hydroxyapatite zeta potential and *Streptococcus mutans* adherence. Infection and Immunity 39(3): 1285-1290.
Reynolds et al., (1984) Effect of casein and whey-protein solutions on caries experience and feeding patterns of the rat. Arch. Oral. Biol. 29(11): 927-933.
Reynolds et al., (1987) Confectionary composition and rat caries. Caries Res. 21: 538-545.
Reynolds et al., (1987) Reduction of chocolate's cariogenicity by supplementation with sodium caseinate. Caries Res. 21: 445-451.
Reynolds et al., (1989), Protein dissimilation by human salivary-sediment bacteria. J. Dent.Res. 68:124-129.
Reynolds et al., "A Review of the Effect of Milk on Dental Caries", Aust. J. Dairy Tech., 34, pp. 175-179 (Dec. 1979).
Reynolds et al., "A Selective Precipitation Purification Procedure for Multiple Phosphoseryl-containing Peptides and Methods for Their Identification", Anal. Biochem., (Mar. 1994), 217:2, pp. 277-284.
Reynolds et al., "Advances in Enamel Remineralization: Anticariogenic Casein Phosphopeptide-Amorphous Calcium Phosphate", J. Clin. Dent. (1999), X(2): pp. 86-88.

(56) References Cited

OTHER PUBLICATIONS

Reynolds et al., "Cariogenicity of a Confection Supplemented with Sodium Caseinate at a Palatable Level." Caries. Res. vol. 23. pp. 368-70 (1989).
Reynolds et al., "Effect of Milk on Caries Incidence and Bacterial Composition of Dental Plaque in the Rat", Arch Oral Biol. (1981) 26:5 pp. 445-451.
Reynolds et al., "Enamel Remineralization by Chewing Gum Containing Casein Phosphopeptide-Amorphous Calcium Phosphate", IADR, General Session, Chiba, Abstract 0489, (2001).
Reynolds et al., "Retention in Plaque and Remineralization of Enamel Lesions by Various Forms of Calcium in a Mouthrinse or Sugar-free Chewing Gum," J Dent Res 82(3): 206-211, 2003.
Reynolds, (1987) The prevention of sub-surface demineralization of bovine enamel and change in plaque composition by casein in an intra-oral model. J. Dental Res. 66(6): 1120-1127.
Reynolds, "Anticariogenic Casein Phosphopeptides", Prot. Peptide Lett. (1999), pp. 295-303.
Reynolds, "Caries Prevention and Oral Health", Health Aspects of Dairy Products/Caries Prevention and Oral Health, 2002. pp. 1306-1313.
Reynolds, "Dairy Components in Oral Health", Aust. J. Dairy Tech. 58: pp. 79-81, (2003).
Reynolds, "The Role of Phosphopeptides in Caries Prevention", Dental Perspectives (1999), 3, pp. 6-7.
Reynolds, 1998, "Anticariogenic complexes of amorphous calcium phosphate stabilized by casein phosphopeptides: A review." Journal of Special Care in Dentistry, vol. 18:1, pp. 8-16.
Reynolds, E. "Calcium phosphate-based remineralizatron systems: scientific evidence?" Australian Dental Journal, vol. 53, 2008, pp. 268-273.
Reynolds, E. C. et al. "Improved plaque uptake and enamel remineralization by fluoride with CPP-ACP." Abstract 2538—84th General Session of the IADR, Jun. 28-Jul. 1, 2006, Brisbane, Australia.
Reynolds, E. C., "Remineralization of Enamel Subsurface Lesions by Casein Phosphopeptide-stabilized Calcium Phosphate Solutions," *J Dent Res.*, 76:9 1587-1595 (1997).
Reynolds, E.C. "Dairy Products and Dental Health," *Proceedings of the Nutrition Society of Australia* pp. 95-102 (1995).
Reynolds, EC et al. "Fluoride and casein phosphopeptide-amorphous calcium phosphate.", J Dent Res vol. 87, No. 4, 2008, pp. 344-348.
Reynolds, EC. "Remineralization of early enamel caries by anti-cariogenic casein phosphopeptide-amorphous calcium phosphate nanocomplexes." Dental Practice Nov./Dec. 2001, 3 pages.
Reynolds, et al., "Anticariogenicity of Calcium Phosphate Complexes of Tryptic Casein Phosphopeptides in the Rat," *J Dent Res*, 74(6): 1272-1279 (1995).
Roberts MJ et al. "Remineralisation of fluorotic enamel lesions by casein phosphopeptide—amorphous calcium 17odems17te17phates (CPP-ACFP) solution." IADR,ANZ division, Abstract 54, 2000.
Roberts, "Role of Models in Assessing New Agents for Caries Prevention-Non-Fluoride Systems", Adv. Dent. Res. (Nov. 1995), 9(3), pp. 304-311; discussion 312-314.
Robinson et al. "Effect of Surface Zone Deproteinisation on the Access of Mineral Ions into Subsurface Carious Lesions of Human Enamel", Caries Res 1990; 24:226-230.
Rose, "Binding Characteristics of *Streptococcus mutans* for Calcium and Casein Phosphopeptide", Caries. Res. (2000), 34, pp. 427-431.
Rose, "Effects of an Anticariogenic Casein Phosphopeptide on Calcium Diffusion in Streptococcal Model Dental Plaques", Arch Oral Biol, vol. 45, Issue 7, (2000) pp. 569-575.
Rosen et al., "Effect of Cheese, With and Without Sucrose, On Dental Caries and Recovery of *Streptococcus mutans* in Rats", J. Dent. Res. 63: pp. 894-896, (1984).
Rozwadowska, E. "Children and private dentistry." Private Dentistry, May 2006, pp. 109-113.

RT Basting, "The Effect of 10% Carbamide Peroxide Bleaching Material on Microhardness of Sound and Demineralized Enamel and Dentin In Situ" Clinical Research, Operative Dentistry, 2001, 26, pp. 531-529.
Sakaguchi, Y. et al. "Preventing acid induced enamel demineralization using CPP-ACP containing paste." Abstract 2055—IADR, Mar. 2005, Baltimore, Maryland, USA.
Sakaguchi, Y. et al. "Remineralization potential of CPP-ACP and its synergy with fluoride," Abstract 191—84th General Session of the IADR, Jun. 28-Jul. 1, 2006, Brisbane, Australia.
Sato et al. "Caries prevention Potential of a Tooth-coating Material Containing Casein Phospho peptide-Amorphous Calcium Phosphate (CPP-ACP)," IADR, General session, Goteborg, 2003, Abstract 1007.
Schüpbach et al., "Incorporation of Caseinoglycomacropeptide and Caseinophosphopeptide into the Salivary Pellicle Inhibits Adherence of Mutans Streptococci", J. Dent. Res, vol. 75, pp. 1779-1788, (1996).
Schweigert, BS et al. "Dental caries in the cotton rat. VI. The effect of the amount of protein, fat and carbohydrate in the diet on the incidence and extent of carious lesions". J. Nutr., vol. 31, 1946, pp. 439-447.
Shaw JH "Effects of dietary composition on tooth decay in the albino rat." J. Nutr. 41, 1950, pp. 13-23.
Sheharyar, S. et al. "Efficacy of MI Paste For Sensitivity Associated With Vital Bleaching," Abstract 2041, IADR Mar. 2007, New Orleans, USA.
Shen et al., "Enamel remineralization by a mouthrinse containing casein phosphopeptide-amorphous calcium phosphate and fluoride in an in situ model"; Australian Dental Journal ADRF; Special Research Supplement, 49(4):S19 (2004).
Shen et al., "Remineralization of Enamel Subsurface Lesions by Sugar-free Chewing Gum Containing Casein Phosphopeptide-Amorphous Calcium Phosphate," J Dent Res 80(12):2066-2070, 2001.
Shen, P. et at. "Remineralization by a mouthrinse containing CPP-ACP at pH 5.5.", Abstract 189—84th General Session of the IADR, Jun. 28-Jul. 1, 2006, Brisbane, Australia.
Silva et al., "Effects of Water-soluble Components of Cheese on Experimental Caries in Humans," J Dent Res 66(1):38-41, Jan. 1987.
Silva, Margarita et al. "Fluoride content of infant formulae in Australia." Australian Dental Journal 1996:41:1. pp. 37-42.
Slomiany, B. et al. "Salivary Mucins in Oral Mucosal Defense", Gen. Pharmac., vol. 27, No. 5, 1996, pp. 761-771.
Smith, S. "Ultramorphological evaluation of dentin after treatment with different desensitizing agents," Abstract 0941, IADR 2007, New Orleans, USA.
Smolenski, D. et al. "MI Paste and Fluoride for Caries Prevention In-Vitro.", Abstract 0505, IADR 2007, New Orleans, USA.
Steinberg, S. "A modern paradigm for caries management, Part 1: Diagnosis and Treatment." Dentistry Today, Feb. 2007.
Steinberg, S. "A modern paradigm for caries management, Part 2: A practical protocol." Dentistry Today, Jun. 2007.
Stößer, L. "Kariesprotektive Eigenschaften des durch Caseinphosphopeptid stabilisierten amorphen Calciumphosphat-Nanokomplexes (CPP-ACP)," Deutsche Zahniirztliche Zeitschrift, vol. 62 (9), pp. 579-588 (2007).
Sudjalim, T.R. et al. Prevention of demineralization around orthodontic brackets in vitro. American Journal of Orthodontics and Dentofacial Orthopedics., 2007, 131, 6, pp. 705.e1-705.E9.
Sudjalim, T.R. et al. "Prevention of white spot lesions in orthodontic practice: a contemporary review.", Australian Dental Journal, vol. 51, No. 4, 2006, pp. 284-289.
Sukasaem, H. et al. "Effect of CPP-ACP on hardness of enamel eroded by Cola-drink." Abstract 1673—84th General Session of the IADR, Jun. 28-Jul. 1, 2006, Brisbane, Australia.
Supplementary European Search Report dated Dec. 13, 2016 in application No. EP 14 83 0019.
Takamizawa, T et al. "Determination of demineralization of tooth substrate by use of an ultrasonic device." Japan J Conserv Dent Jun vol. 47 Spring Issue 24—Abstract B-4, 2004.

(56) References Cited

OTHER PUBLICATIONS

Talbo et al., "MALDI-PSD-MS Analysis of the Phosphorylation Sites of Caseinomacropeptide", Peptides (Jul. 2001) 22:7, pp. 1093-1098.
Tantbirojn, D. et al. "Changes in surface hardness of enamel by a cola drink and CPP-ACP paste," Journal of Dentistry, vol. 36, 2008, pp. 74-79.
Tay et al. "Assessing the Effect of a Desensitizing Agent Used Before In-office Tooth Bleaching," The Journal of the American Dental Association, vol. 140, Issue 10, (Oct. 2009); pp. 1245-1251.
Ten Cate, Jacob M. "Current concepts on the theories of the mechanism of action offluoride." Acta Odontol, Scand 57 (1999), 325-329.
Theerapiboon, U. et al. "Remineralization of artificial caries by CPP-ACP paste.", Abstract 3274, Jul. 2008, International Association for Dental Research, Toronto, Canada.
Trajtenberg, C.P. et al. "CPP-ACP Paste with Fluoride: In Vitro Root Surface Caries Formation," Abstract 0500, IADR 2007 New Orleans, USA.
Translation of Japanese Office Action from Application No. 2002-590925, dated Nov. 18, 2008.
Translation of Russian Office Action from Application No. 2007123603, dated May 26, 2009.
Turssi, C.P. et al. "Progression of erosion following use of calcium and phosphorus compounds.", Abstract 2499, Jul. 2008, International Association for Dental Research, Toronto, Canada.
Ung, M. et al. "Investigation of the binding of casein phosphopeptides to the major enamel pellicle proteins.", Australian Dental Journal ADRF Special Research Supplement vol. 49, No. 4, S19-S20, 2004.
Vb Haywood, "History, safety, and effectiveness of current bleaching techniques and applications of the nightguard vital bleaching technique" Quintessence Int. Jul. 1992; 23(7): 471-88. (Year: 1992).
Vlacic et al., "Combined CPP-ACP and photoactivated disinfection (PAD) therapy in arresting root surface caries: a case report"; British Dental Journal; 203(8):457-459 (2007).
Walker et al., "Consumption of milk with added casein phosphopeptide-amorphous calcium phosphate remineralizes enamel subsurface lesions in situ," Australian Dental Journal, vol. 54, No. 3, pp. 245-249, Sep. 2009.
Walker, Glen et al. "Increased remineralization of tooth enamel by milk containing added casein phosphopeptide amorphous calcium phosphate." Journal of Dairy Research (2006) 73, pp. 74-78.
Walsh, "Tooth Mousse Information," GC Tooth Mousse Portfolio $2^{nd}$ Edition, Mar. 2005.
Walsh, L. "Application of the System for Total Environmental Management (STEM) to demineralization, dental erosion and tooth wear," Australasian Dental Practice, Jan.-Feb. 2008, pp. 52-58.
Walsh, L.J. "The effects of GC Tooth Mousse on cervical dentinal sensitivity: a controlled clinical trial", International Dentistry SA—Australasian Edition vol. 12, No. 1, 4-12, 2010.
Walsh, L.J. et al. "Effect of CPP-ACP versus potassium nitrate on cervical dentinal hypersensitivity," Abstract 947—$84^{th}$ General Session of the IADR, Jun. 28-Jul. 1, 2006, Brisbane, Australia.
Weiss, Dr. V. "Kariesprophylaxe in der kinderzahnnärztlichen Praxis", ZWP, Oct. 2005, 18 pp. 76-79. English Abstract.
Westerman, G. et al. "Argon Laser and Remineralizing Paste Effect on Root Surface Caries," Abstract 0018, IADR Mar. 2007, New Orleans, USA.
Westerman, G. et al., "The Argon Laser and Remineralizing Paste with Fluoride Effects on Enamel Caries," AAPD, Washington, 2008.
White, "Use of Synthetic Polymer Gels for Artificial Carious Lesion Preparation" Caries Research 21, 1987, pp. 228-242. Abstract Only.
Wilfershausen, B. et al. "In-Vitro-Studie Zur Überprüfung einermöglichen Remeralisation durch caesinphosphopetidhaltige Calciumphosphat-komplexe (CPP ACP).", Deutsche Zahnarztiche Zeitschrift, vol. 63, No. 2, 2008, pp. 134-139. English Abstract.
Wilkiel, et al., "Hydroxyapatite Mineralization and Demineralization in the Presence of Synthetic Phosphorylated Pentapeptides," Archives of Oral Biology, 39:8, 715-721 (1994).

William, V. et al. "Molar Incisor Hypomineralization: Review and Recommendations for Clinical Management", Pediatric Dentistry, vol. 28, No. 3, 224-232, 2006.
Wong, L. et al. "Plaque microcosm biofilm mineralization by CPP-ACP and calcium-phosphatemonofluorophosphate-urea mineralizing solution." Abstract 1269—$84^{th}$ General Session of the IADR, Jun. 28-Jul. 1, 2006, Brisbane, Australia.
Wong, R. et al. Incorporation of casein phosphopeptide-amorphous calcium phosphate into a temporary cement. Abstract 0653—$84^{th}$ General Session of the IADR, Jun. 28-Jul. 1, 2006, Brisbane, Australia.
Wright, S. et al. "Artificial Caries Inhibited with MI Paste and Two Restorative Materials," Abstract 2777, IADR 2007, New Orleans, USA.
Xie, Q. et al. "Remineralization Effects of CPP-ACP and Proanthocyanidin on Artificial Root Caries," Abstract 0512, IADR 2007, New Orleans, USA.
Yamaguchi, K. et al. "Effect of CPP-ACP paste on mechanical properties of bovine enamel as determined by an ultrasonic device," Journal of Dentistry, vol. 34, 2006, pp. 230-236.
Yamaguchi, K. et al. "Ultrasonic determination of the effect of casein phosphopeptide-amorphous calcium phosphate paste on the demineralization of bovine dentin," Caries Res, vol. 41, 2007, pp. 204-207.
Zero, "Dentifrices, mouthwashes, and remineralization/caries arrestment strategies," BMC Oral Health, vol. 6 (Suppl I)S9, pp. 1-13 (Jul. 2010).
Zero, DT "In situ caries models." Adv Dent Res vol. 9(3), 1995, pp. 214-230.
Zhang, L, et al. "Experimental study of phosphopeptide in promoting tooth remineralisation." Chinese J Dent Res., vol. 3(1), May 2000, pp. 27-30.
Zhao et al. "The remineralization for enamel lesions by casein phosphopeptide-amorphous calcium fluoride 21odems21te in vitro." Zhonghua Kou Qiang Yi Kxue Za Zhi. vol. 36. No. 6. 2001. pp. 421-423, with English translation.
Colgate, Fluoride Conversions, Colgate professional.com (Feb. 2013).
Mitthra et al., "Mineral Loss before and after .Bleaching and Mineral Uptake on Application of Remineralizing Agent", Indian Journal of Multidisciplinary Dentistry and Endodontics, vol. 1, No. 1, Jan. 2010.
De Oliveira et al. "In situ effect of a CPP-ACP chewing gum on enamel erosion associated or not with abrasion"; Clin Oral Investig. 21:339-346 (Mar. 2016).
Farooq et al., "A review of novel dental caries preventative material: Casein phosphoepetide-amorphous calcium phosphate (CPP-ACP) complex," King Saud University Journal of Dental Sciences (2013) 4, 47-51.
Sim et al., "Anti-caries effect of CPP-ACP in irradiated nasopharyngeal carcinoma patients," Clinical Oral Investigations vol. 19, No. 5, pp. 1005-1011 (2015).
Denes et al., "Oxidation of SnF2 stannous fluoride in aqueous solutions," Hyperfine Interact 90: 435-439 (1994).
Google scholar search_Sep. 21, 2020_GC Tooth Mousse periodontitis (2020).
Google scholar serach_Sep. 21, 2020_oral dysbiosis (2020).
Google Search_Sep. 22, 2020_removing supragingival bacteria with brushing (2020).
Kilian et al., "The oral microbiome-an update for oral healthcare professionals," British Dental Journal, vol. 221, No. 10, pp. 657-666 (Nov. 2016).
Martinez-Pablon et al., "Comparison of the Effect of Two Sugar-Substrate Chewing Gums on Different Caries- and Gingivitis-Related Variables: a Double-Blind, Randomized, Controlled Clinical Trial," Clinical Oral Investigations (2014) 18: 589-598.
Sakr et al., "The Effect of Recaldent (CPP-ACP) on the most putative bacteria in caries and chronic gingivitis," Ain Shams Dental Journal, vol. X, No. 2 pp. 211-219 (Jun. 2007).
Zanatta et al., "Supragingival Plaque Removal with and without Dentifrice: A Randomized Controlled Clinical Trial," Braz Dent J, vol. 23, No. 3, pp. 235-240 (2012).

(56) References Cited

OTHER PUBLICATIONS

Chen, Y. et al. "Research progress of complex of casein phosphopeptide and amorphous calcium phosphate in oral therapy", Chin. J. Aesth. Med., vol. 23, No. 8, pp. 681-683 (2014).

Ying, S.N. & Liu, L. "Research progress of enamel remineralization materials [J/CD]", Chin. J. Stomatol. Res. (Electronic version), vol. 5 No. 1, pp. 94-99 (2011).

Madhavan, S et al., "Dentinal hypersensitivity: A comparative clinical evaluation of CPP-ACPF, sodium fluoride, propolis, and placebo", Journal of Conservative Dentistry, 2012; 15(4): 315-318.

* cited by examiner

C

TREATMENT FOR PERIODONTITIS

CROSS-REFERENCE TO RELATED APPLICATIONS

This application is the U.S. National Stage of International Application PCT/AU2018/050231, filed Mar. 14, 2018, and claims priority from Australian provisional application no. 2017900893, filed Mar. 14, 2017, the entire contents of which are incorporated by reference in their entirety.

FIELD OF THE INVENTION

The present invention relates to compositions and their use for oral care. In particular, the compositions and methods are for maintaining oral health and/or treating various oral conditions such as gingivitis.

BACKGROUND OF THE INVENTION

Oral microbes have co-evolved and co-existed with their hosts for millions of years in a mostly harmonious symbiotic relationship. The host and oral microbiome are not distinct entities but together form a 'superorganism' or holobiont, with the oral microbiome playing a significant role in the maintenance and health of the oral cavity. The mouth provides an environment for the second most diverse microbial community in the body, with over 700 resident species of bacteria that colonise the hard surfaces of teeth and the soft tissues of the oral mucosa. Through recent advances in DNA sequencing technology the complexities of the oral microbiome have been revealed which has provided new insights into the role of the different intra-oral polymicrobial biofilms during both health and disease.

Many of the bacterial species associated with health were thought of as only commensal organisms but through this greater insight it is clear now that many are in fact beneficial to their hosts. These commensal/beneficial species are now referred to as symbionts as they are in a true symbiotic relationship with their host providing essential factors to improve health and/or preventing pathogenic species from colonizing to cause disease. However, perturbations of the oral microbiome through modern-day lifestyles (e.g. dietary sugar, smoking, poor oral hygiene etc) or other factors (e.g. genetic predisposition) can have detrimental consequences for general and oral health. The finely-tuned equilibrium (homeostasis or symbiosis) of the oral ecosystem can then be disrupted, allowing disease-promoting bacteria (pathobionts) to outcompete the beneficial/commensal symbionts to manifest dysbiosis and cause diseases such as periodontal diseases (gingivitis and periodontitis). Hence it is essential to promote a balanced oral microbiome to effectively maintain or restore oral health. The process of promotion of beneficial/commensal symbionts to produce a balanced oral microbiome and homeostasis is referred to as prebiosis. Hence substances which promote a balanced oral microbome and homeostasis by increasing the proportions of symbiotic bacteria are referred to as prebiotics.

Casein phosphopeptide-amorphous calcium phosphate (CPP-ACP) is a salivary biomimetic which provides bioavailable calcium and phosphate ions to remineralise early stages of dental caries in enamel and dentine. Specific complexes of casein phosphopeptides and amorphous calcium phosphate ("CPP-ACP", available commercially as Recaldent™) have been shown to remineralize enamel subsurface lesions in vitro and in situ.

WO 98/40408 in the name of The University of Melbourne (the contents of which are herein incorporated fully by reference) describes casein phosphopeptide-amorphous calcium phosphate complexes (CPP-ACP) and CPP-stabilised amorphous calcium fluoride phosphate complexes (CPP-ACFP) which have been produced at alkaline pH. Such complexes have been shown to promote remineralization of enamel subsurface lesions in animal and human in situ caries models. Moreover, improvements on these compositions are disclosed in WO 2006/066013 and WO 2007/090242 and specific uses (the contents of which are herein incorporated fully by reference).

There is a need for new or improved treatments for diseases of the gingiva. In addition, there is a need for new or improved therapies to maintain or restore gingival health.

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

SUMMARY OF THE INVENTION

In one aspect, the present invention provides a method for reducing pathogenic oral bacteria at an oral site in an individual, the method comprising administering stabilized amorphous calcium phosphate (ACP) and/or stabilized amorphous calcium fluoride phosphate (ACFP) to the oral cavity of the individual, thereby reducing pathogenic bacteria at an oral site.

In another aspect, the present invention also provides a method for increasing commensal oral bacteria at an oral site in an individual, the method comprising administering stabilized amorphous calcium phosphate (ACP) and/or stabilized amorphous calcium fluoride phosphate (ACFP) to the oral cavity of the individual, thereby increasing commensal oral bacteria at an oral site.

In another aspect, the present invention also provides a method of decreasing the proportion of pathogenic oral bacteria at an oral site in an individual, the method comprising administering stabilized amorphous calcium phosphate (ACP) and/or stabilized amorphous calcium fluoride phosphate (ACFP) to the oral cavity of the individual, thereby reducing the proportion of pathogenic oral bacteria at an oral site.

In any aspect of the invention described herein, the pathogenic oral bacteria may be any one or more associated with gingival inflammation, gingivitis, chronic gingivitis, periodontitis or periodontal disease. Typically, the pathogenic oral bacteria are acidogenic and/or aciduric and/or inflammogenic. Preferably, the bacteria are inflammogenic. Bacteria that produce lipopolysaccharide (LPS) and release LPS into the tissues as LPS are highly inflammogenic.

Preferably, the bacteria are any one or more selected from *Streptococcus mutans, Actinomyces naeslundii, Veillonella parvula, Lactobacillus casei, Porphyromonas gingivalis, Tannerella forsythia, Treponema denticola, Leptotrichia wadei, Leptothrichia shahii, Leptotrichia buccalis* and *Lautropia mirabilis*.

In any aspect of the invention described herein, the commensal oral bacteria may be any one or more species that express arginine deiminase and/or nitrate reductase. Typically, the bacteria are any one or more of *Corynebacterium durum, Rothia dentocariosa, Streptococcus mitis, Streptococcus sanguinis* and *Fusobacterium nucleatum*.

In one aspect, the present invention provides a method of inhibiting oral dysbiosis, the method comprising administering stabilized amorphous calcium phosphate (ACP) and/or stabilized amorphous calcium fluoride phosphate (ACFP) to the oral cavity of the individual, thereby inhibiting oral dysbiosis.

In another aspect, the present invention provides a method of reducing gingival inflammation in an individual in need thereof, the method comprising administering stabilized amorphous calcium phosphate (ACP) and/or stabilized amorphous calcium fluoride phosphate (ACFP) to the oral cavity of the individual, thereby reducing gingival inflammation. Preferably, the method further comprises an initial step of identifying an individual having gingival inflammation.

In another aspect, the present invention provides a method of treating gingivitis in an individual in need thereof, the method comprising administering stabilized amorphous calcium phosphate (ACP) and/or stabilized amorphous calcium fluoride phosphate (ACFP) to the oral cavity of the individual, thereby treating gingivitis. Preferably, the method further comprises an initial step of identifying an individual having gingivitis.

In another aspect, the present invention provides a method of treating chronic gingivitis in an individual in need thereof, the method comprising administering stabilized amorphous calcium phosphate (ACP) and/or stabilized amorphous calcium fluoride phosphate (ACFP) to the oral cavity of the individual, thereby treating chronic gingivitis. Preferably, the method further comprises an initial step of identifying an individual having chronic gingivitis.

In another aspect, the present invention provides a method of treating periodontitis in an individual in need thereof, the method comprising administering stabilized amorphous calcium phosphate (ACP) and/or stabilized amorphous calcium fluoride phosphate (ACFP) to the oral cavity of the individual, thereby treating periodontitis. Preferably, the method further comprises an initial step of identifying an individual having periodontitis.

In any aspect of the invention, the method further comprises performing a dental procedure prior to administering stabilized amorphous calcium phosphate (ACP) and/or stabilized amorphous calcium fluoride phosphate (ACFP) to the oral cavity of the individual. Examples of dental procedures include debridement, scaling, root planning or any other procedure to remove subgingival or supragingival bacteria.

In another aspect, the present invention provides use of stabilized amorphous calcium phosphate (ACP) and/or stabilized amorphous calcium fluoride phosphate (ACFP) in the preparation of a medicament for:
  reducing pathogenic oral bacteria at an oral site in an individual;
  increasing commensal oral bacteria at an oral site in an individual;
  decreasing the proportion of pathogenic oral bacteria at an oral site in an individual
  inhibiting oral dysbiosis;
  reducing gingival inflammation in an individual in need thereof;
  treating gingivitis in an individual in need thereof; or
  treating chronic gingivitis in an individual in need thereof.

In another aspect, the present invention provides stabilized amorphous calcium phosphate (ACP) and/or stabilized amorphous calcium fluoride phosphate (ACFP) for use in:
  reducing pathogenic oral bacteria at an oral site in an individual;
  increasing commensal oral bacteria at an oral site in an individual;
  decreasing the proportion of pathogenic oral bacteria at an oral site in an individual
  inhibiting oral dysbiosis;
  reducing gingival inflammation in an individual in need thereof;
  treating gingivitis in an individual in need thereof; or
  treating chronic gingivitis in an individual in need thereof.

In another aspect, the present invention provides a method for reducing demineralization of dental enamel in an individual, the method comprising administering stabilized amorphous calcium phosphate (ACP) and/or stabilized amorphous calcium fluoride phosphate (ACFP) to the oral cavity of the individual, thereby reducing demineralization of dental enamel in an individual. Preferably, the stabilised ACP complex is a stannous-associated phosphopeptide (PP) stabilized amorphous calcium phosphate (ACP) complex, and the stabilised ACFP complex is a stannous-associated phosphopeptide (PP) stabilized amorphous calcium fluoride phosphate (ACFP) complex. Preferably, the reduction in demineralization is a reduction in the rate of demineralization.

Preferably, the stabilized amorphous calcium phosphate (ACP) and/or amorphous calcium fluoride phosphate (ACFP) is phosphopeptide stabilized. Preferably, the phosphopeptide (as defined below) is a casein phosphopeptide.

In any method or use of the invention, the stabilised ACP or ACFP complex may be administered to the individual for 5 to 60 minutes, 10 to 45 minutes, 10 to 30 minutes or 20 minutes. Further, the stabilised ACP or ACFP complex may be administered 4, 5 or 6 times per day, or per 24 hour period. Preferably, the stabilised ACP or ACFP complex is administered for a 1 to 2 week period.

In any aspect, the composition may be prepared and used in various forms applicable to the mouth such as dentifrice including toothpastes, toothpowders and liquid dentifrices, mouthwashes, mouthrinses, mouth sprays, varnish, dental cement, troches, chewing gums, dental pastes, gingival massage creams, gargle tablets, dairy products and other foodstuffs including yoghurt. Preferably, the composition is a chewing gum. Preferably, the chewing gum contains at least about 15 mg, 20 mg, 25 mg, 30 mg, 35 mg, 40 mg, 45 mg, 50 mg, 55 mg or 60 mg of stabilised ACP or ACFP complex. The chewing gum may contain about 18.8 or 56.4 mg of stabilised ACP or ACFP complex.

In any aspect, the calcium ion content of the stabilised ACP or ACFP complex is greater than about 30 moles per mole of PP. Preferably, the calcium ion content is in the range of about 30 to 100 moles of calcium per mole of PP. More preferably, the calcium ion content is in the range of about 30 to about 50 moles of calcium per mole of PP.

In any aspect, the stabilised ACP complex is a stannous-associated phosphopeptide (PP) stabilized amorphous calcium phosphate (ACP) complex, and the stabilised ACFP complex is a stannous-associated phosphopeptide (PP) stabilized amorphous calcium fluoride phosphate (ACFP) complex.

In any aspect, the ACP and/or ACFP complex is in the form of a casein phosphopeptide stabilized ACP and/or ACFP complex.

Preferably, the phase of the ACP is primarily (i.e. >50%) a basic phase, wherein the ACP comprises predominantly the species $Ca^{2+}$, $PO_4^{3-}$ and $OH^-$. The basic phase of ACP may have the general formula $[Ca_3(PO_4)_2]_x[Ca_2(PO_4)(OH)]$ where $x \geq 1$. Preferably $x=1-5$. More preferably, $x=1$, i.e. the two components of the formula are present in equal proportions. Accordingly, in one embodiment, the basic phase of ACP has the formula $Ca_3(PO_4)_2Ca_2(PO_4)(OH)$.

Preferably, the phase of the ACFP is a primarily (i.e. >50%) basic phase, wherein the ACFP comprises predominantly the species $Ca^{2+}$, $PO_4^{3-}$ and $F^-$. The basic phase of ACFP may have the general formula $[Ca_3(PO_4)_2]_x[Ca_2(PO_4)F]_y$, where $x \geq 1$ when $y=1$ or where $y \geq 1$ when $x=1$. Preferably, $y=1$ and $x=1$-3. More preferably, $y=1$ and $x=1$, i.e. the two components of the formula are present in equal proportions. Accordingly, in one embodiment, the basic phase of ACFP has the formula $Ca_3(PO_4)_2Ca_2(PO_4)F$.

In one embodiment, the ACP complex consists essentially of phosphopeptides, calcium, phosphate and hydroxide ions and water. Preferably, the complex further includes stannous ions.

In one embodiment, the ACFP complex consists essentially of phosphopeptides, calcium, phosphate, fluoride and hydroxide ions and water. Preferably, the complex further includes stannous ions.

The invention also relates to a kit for use in a method or use of the invention, the kit comprising:
(a) a composition as described herein, or
(b) a stabilized ACP or ACFP complex as described herein.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

DETAILED DESCRIPTION OF THE EMBODIMENTS

Figure 1:
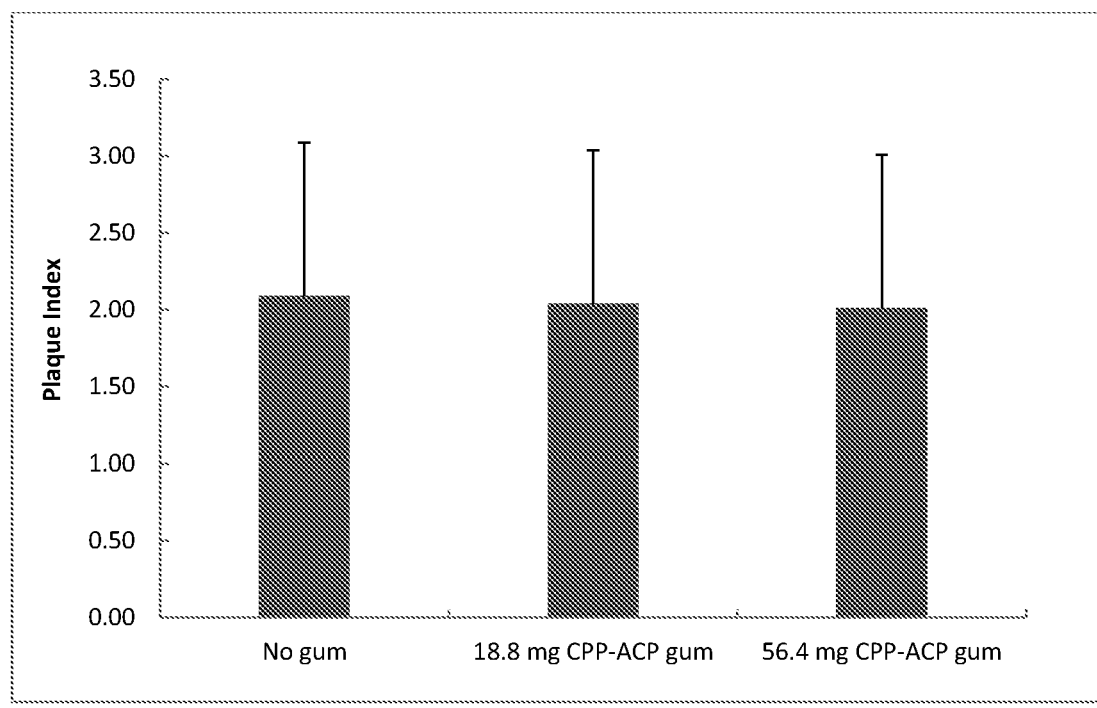
FIG. 1. Effect of CPP-ACP on plaque index in a randomised, controlled clinical trial.

It will be understood that the invention disclosed and defined in this specification extends to all alternative combinations of two or more of the individual features mentioned or evident from the text or drawings. All of these different combinations constitute various alternative aspects of the invention.

Further aspects of the present invention and further embodiments of the aspects described in the preceding paragraphs will become apparent from the following description, given by way of example and with reference to the accompanying drawings.

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

All of the patents and publications referred to herein are incorporated by reference in their entirety.

For purposes of interpreting this specification, terms used in the singular will also include the plural and vice versa.

As used herein, except where the context requires otherwise, the term "comprise" and variations of the term, such as "comprising", "comprises" and "comprised", are not intended to exclude further additives, components, integers or steps. As used herein, except where the context requires otherwise, "comprise" and "include" can be used interchangeably.

The present invention is based on the unexpected finding that stabilized amorphous calcium phosphate forms, such as CPP-ACP, CPP-ACFP or stannous-associated ACP or ACFP, can reduce gingival inflammation and treat various gingival conditions such as gingivitis. While stabilized amorphous calcium phosphate forms have previously been shown to remineralize dental lesions by delivering calcium and phosphate to form crystalline hydroxyapatite or fluorapatite in the tooth lesion, these stabilized amorphous calcium phosphate forms have now been shown to surprisingly have an effect on the beneficial and pathogenic oral bacteria present in the oral cavity and the tissue (i.e. gingiva) in the oral cavity. Even more surprisingly, the stabilized amorphous calcium phosphate forms increase the relative abundance of beneficial oral bacteria while reducing the relative abundance of pathogenic oral bacteria. Without being bound by any theory or mode of action, it is this differential effect on oral bacteria that appears to result in a reduction in gingival inflammation.

Any method of the invention may involve the treatment of an oral site in an individual where the oral site is any one or more regions around a tooth including disto-buccal, mid-buccal, mesio-buccal, mesio-palatal, mid-palatal and disto-palatal and disto-lingual, mid-lingual and mesio-lingual. The treatment may be applied directly to the gingiva and no other site in the oral cavity. The treatment may be of multiple oral sites. Alternatively, the entire oral cavity may be treated. Further, efficacy of the treatment may be determined by analysis of one or more oral sites or the entire oral cavity. For example, a reduction in pathogenic bacteria or an increase in commensal bacteria may be determined by analysis of one or more oral sites as described herein or by analysis of the entire oral cavity.

In any aspect of the invention, the individual is one in need of treatment or prevention. Specifically, in any aspect of the invention, the method or use further comprises a step of identifying an individual in need of treatment or prevention.

An individual in need of treatment to reduce pathogenic oral bacteria or increase commensal oral bacteria may be one who has, or who is experiencing, perturbations of the oral microbiome through modern-day lifestyles (e.g. excessive dietary sugar intake, smoking, poor oral hygiene) or other factors (e.g. genetic predisposition).

In any aspect of the invention, the individual may not have any dental lesions. For example, the individual may be identified as having gingival inflammation or gingivitis but no detectable dental surface or subsurface lesions.

The words 'treat' or 'treatment' refer to therapeutic treatment wherein the object is to slow down (lessen) an undesired physiological change or disorder. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. Treatment may not necessarily result in the complete absence of detectable symptoms of the condition but may reduce or minimise complications and side effects of the condition. The success or otherwise of treatment may be monitored by physical examination of the individual, cytopathological, serological DNA, mRNA detection techniques, or any other techniques described herein.

The words 'prevent' and 'prevention' generally refer to prophylactic or preventative measures for protecting or precluding an individual not having gingival inflammation or any other condition described herein from progressing to that complication. Individuals in which prevention is required include those who have dysbiosis.

The phrase 'pharmaceutically acceptable' indicates that the substance or composition must be compatible chemically and/or toxicologically, with the other ingredients comprising a formulation, and/or the individual being treated therewith.

The methods of the invention are applicable to individuals that manifest sub clinical or clinical symptoms of a disease or condition of oral tissue as described herein.

Dysbiosis in an individual means the individual has, in the context of a randomly selected cohort of individuals, an abnormal total amount or relative abundance of microbial pathogens in the oral cavity. For example, the individual may have elevated amounts or proportion of one or more pathogenic bacteria associated with gingival inflammation, gingivitis, chronic gingivitis, periodontitis or periodontal disease. Typically, the pathogenic bacteria are acidogenic and/or aciduric and/or inflammogenic. Preferably, the bacteria are any one or more selected from *Streptococcus mutans, Actinomyces naeslundii, Veillonella parvula, Lactobacillus casei, Porphyromonas gingivalis, Tannerella forsythia* and *Treponema denticola*.

The symptoms of gingival inflammation may be manifested in oral tissue of said individual at one or more oral sites. The cellular hallmarks of inflammation that may be present include an increased movement of plasma and leukocytes from the blood into the injured tissues. Clinical signs of gingival inflammation may also be present including rubor (redness), calor (increased heat), tumor (swelling), dolor (pain), and functio laesa (loss of function). Chronic inflammation may be characterised by leukocyte cell (monocytes, macrophages, lymphocytes, plasma cells) infiltration. Tissue and bone loss may be observed. Examples of inflammation include gingivitis.

Reducing gingival inflammation may be a reduction in the incidence and/or severity of inflammation of the gingiva. This may be determined by a reduction in the incidence or severity of any clinical, cellular or biochemical characteristics as described herein, such as those outlined immediately above.

In further embodiments, the individual may present with chronic inflammation of oral tissue. In one example the individual may present with gingivitis (such as chronic gingivitis), resorption of alveolar bone and eventual tooth loss stemming from progressive loss of collagen attachment of the tooth to alveolar bone. Other lesions of mucosal or related oral tissue are possible.

In any aspect, an individual in need thereof may be one who is identified as having mild, moderate or severe gingival inflammation. As chronic gingivitis can lead to the more severe periodontitis the invention could also be applicable to those with mild, moderate and severe periodontitis as determined by CDC-AAP methodology described in Eke et al J Dent Res 91:914-920 (2012). The invention is also applicable to individuals with gingival inflammation identified using the Modified Gingival Index (Lobene et al 1986 Clin Prev Dent. January-February; 8(1):3-6). This index is a modification of the Löe and Silness Gingival Index and allows greater discrimination for mild and moderate gingivitis. The individual may be determined to have gingival inflammation on a scale from 0 to 4 for gingival tissues associated with one or more sites (e.g. buccal, lingual, mesial and distal). Preferably, the individual in need thereof has a Modified Gingival Index score of 1, 2, 3 or 4. Accordingly, in any aspect of the invention, an individual is provided that has a degree of gingival inflammation as described herein. In any aspect of the invention, the method or use further comprises the step of determining whether an individual has a degree of gingival inflammation as described herein.

Identifying an individual in need of a reduction in pathogenic oral bacteria, increase commensal oral bacteria, or who has oral dysbiosis may be determined by the amount of, or relative proportions of, bacteria in a sample obtained from oral fluid taken from the oral cavity. In particular, an oral fluid may be saliva, gingival crevicular fluid or blood. It is recognized that oral fluids, for example saliva, are a combination of secretions from a number of sources such as parotid, submandibular, sublingual, accessory glands, gingival mucosa and buccal mucosa and the term oral fluid includes the secretion of each of these sources individually or in combination. The saliva may be stimulated or in a preferred embodiment unstimulated. Stimulation of the saliva in the individual may occur by allowing the individual to chew on sugar-free gum, a piece of paraffin film or tart candy. Unstimulated saliva means that the individual will expectorate into a collection vessel without stimulation of salivary flow.

Saliva specimens for testing can be collected following various methods known in the art, for example, stimulated or unstimulated saliva can be sampled by the individual expectorating into a collection vessel or using a swab or syringe to extract the saliva. Other ways for obtaining unstimulated saliva are known in the art. (Nazaresh and Christiansen, J. Dent. Res. 61: 1158-1162 (1982)). Methods and devices for collecting saliva have also been described. (See also, U.S. Pat. No. 5,910,122).

It is contemplated that the methods of the present invention can also be practiced by analyzing stimulated saliva.

Furthermore, the methods of the present invention are not limited to performing salivary analysis immediately after collection of the sample. In certain embodiments, salivary analysis following the methods of the present invention can be performed on a stored saliva sample. The saliva sample for testing can be preserved using methods and apparatuses known in the art. (See e.g., U.S. Pat. No. 5,968,746).

It is also contemplated that the methods of the present invention be used to perform salivary analysis on saliva samples that have been treated to reduce its viscosity.

The viscous nature of saliva, due to the nature of mucopolysaccharides, makes testing of these fluids difficult. In order to prepare saliva for any laboratory testing procedure, the saliva may be rendered sufficiently fluid (i.e. viscosity must be reduced) and free from debris. Techniques used to remove debris include centrifugation and filtration. The viscosity of saliva can also be reduced by mixing a saliva sample with a cationic quaternary ammonium reagent. (See, U.S. Pat. No. 5,112,758).

In another embodiment, the sample from an individual may be taken from the crypts of the dorsum of the tongue.

The sample from the individual may be taken from a specific periodontal site. A periodontal site is a region within the oral cavity. Preferably, a periodontal site is region around a tooth including disto-buccal, mid-buccal, mesio-buccal, mesio-palatal, mid-palatal and disto-palatal and disto-lingual, mid-lingual and mesio-lingual. The sample may be taken from a periodontal site that exhibits clinical signs of inflammation.

In another embodiment, the sample from an individual may be a sample of a tissue. The tissue or part thereof may be from the oral cavity. In certain embodiments the tissue is gingival. The gingival tissue may be from various sites around a tooth including disto-buccal, mid-buccal, mesio-buccal, mesio-palatal, mid-palatal and disto-palatal and disto-lingual, mid-lingual and mesio-lingual. The tissue may be obtained by normal biopsy or may be obtained from an extracted tooth.

In another embodiment the sample from the individual may be dental plaque. The plaque may be subgingival or supragingival. Subgingival plaque may be sampled using a sterile curette or paper point. Supragingival plaque may be removed using standard techniques known in the art. The subgingival plaque may be collected from various sites around a tooth including disto-buccal, mid-buccal, mesio-buccal, mesio-palatal, mid-palatal and disto-palatal and disto-lingual, mid-lingual and mesio-lingual periodontal sites. The subgingival plaque samples may be obtained during the normal dental examination provided by a qualified dentist or periodontist. The plaque sample may be analysed as is or treated to extract the protein, peptide or fragment thereof of interest using an extraction buffer. An extraction buffer could contain a pH buffer (e.g. phosphate, HEPES, etc), salts (e.g. NaCl) to maintain ionic strength and protein solubilising agents (e.g. detergents (SDS, Triton X100, etc)), reducing agents (e.g. dithiothreitol, cysteineHCl) and/or chaotropic agents (e.g. urea, guanidinium chloride, lithium perchlorate).

Dysbiosis may be determined by comparing the amount or, or relative proportion of, pathogenic and/or commensal oral bacteria a sample from an individual and comparing it with a set of parameters previously defined from individuals that do not have attributes of an individual with dybiosis or any clinical, cellular or biochemical characteristics of gingival inflammation. It is contemplated that individuals with a healthy oral cavity may contain a low level of pathogenic bacteria present. This low level or normal level of pathogenic bacterial colonisation does not indicate dysbiosis. When using such a control and comparing it to a test sample, determination of whether an individual has dysbiosis includes (1) an elevated level of one or more pathogenic bacteria as described herein in a sample taken from the individual compared to the control sample, or (2) an increased proportion of one or more pathogenic bacteria in a sample taken from the individual compared to the total level of bacteria in the control sample, or (3) an increased proportion of one or more pathogenic bacteria relative to one or more other bacteria species in a sample taken from the individual when compared with the control sample.

A stabilized-ACP or ACFP complex as referred to herein include a stabilized-ACP or ACFP complex as described in PCT/AU2005/001781 the contents of which are incorporated by reference.

In a preferred embodiment, the phosphopeptide stabilised amorphous calcium phosphate (ACP) or amorphous calcium fluoride phosphate (ACFP) complex has tightly bound and loosely bound calcium, wherein the bound calcium in the complex is less than the tightly bound calcium in an ACP or ACFP complex formed at a pH of 7.0. Optionally, the ACP or ACFP is predominantly in a basic form.

A stabilized-ACP or ACFP complex as referred to herein include a stabilized-ACP or ACFP complex formed at a pH of below 7.0. Preferably the complex is formed at a pH in the range of about 5.0 up to but below 7.0. More preferably the complex is formed at a pH range of about 5.0 to about 6.0. In a preferred embodiment, the complex is formed at a pH of about 5.5. Preferably, the ACP or ACFP in the complex is predominantly in a basic form.

A stabilized-ACP may be produced by a method comprising the steps of:
(i) obtaining a solution comprising at least one phosphopeptide and;
(ii) admixing solutions comprising calcium ions, phosphate ions and hydroxide ions, while maintaining the pH at about 7.0 or below.

A stabilised ACFP may be produced by a method comprising the steps of:
(i) obtaining a solution comprising at least one phosphopeptide and;

(ii) admixing solutions comprising calcium ions, phosphate ions, hydroxide ions and fluoride ions, while maintaining the pH at about 7.0 or below.

A phosphopeptide stabilised amorphous calcium phosphate (ACP) or amorphous calcium fluoride phosphate (ACFP) complex may also include wherein the ACP in the complex has tightly bound and loosely calcium, wherein the tightly bound calcium in the complex is less than the tightly bound calcium in an ACP or ACFP complex formed at a pH of 7.0 and the ACP or ACFP is predominantly in a basic form, obtainable or obtained by a method comprising:
a) admixing a first solution comprising calcium ions, a second solution comprising phosphate ions, and optionally a third solution comprising fluoride ions, to a solution comprising phosphopeptides and a solvent with a pH of from about 5 up to but below 7; and
b) maintaining the pH of the solution at about 5.0 up to but below 7.0 during the admixing by adding hydroxide ions.

"Tightly" and "loosely" bound calcium and phosphate in ACP or ACFP can be determined using analytical ultrafiltration. Briefly, the solution of phosphopeptide, calcium, phosphate and optionally fluoride admixed while maintaining the pH at about 7.0 or below can be first filtered through a 0.1 micron filter to remove free calcium and phosphate that is not associated with the complexes. This free calcium and phosphate is present in the filtrate and discarded. Any free calcium or phosphate that is not associated in any way with the complexes would not be bioavailable, i.e. delivered by the phosphopeptide to the tooth. The retentate from the 0.1 micron filtration can be further analyzed by centrifugation through a 3000 mw cutoff filter at 1,000 g for 15 min. The resulting filtrate contains calcium and phosphate that is loosely bound or associated with the complexes. At this centrifugal force calcium and phosphate that is not tightly bound to the complexes are released and move to into the filtrate. The Ca and Pi that is tightly bound in the complexes is retained in the retentate. The amount of tightly bound Ca and Pi in the retentate can then be determined by subtracting the amount of Ca and Pi in the filtrate from the total amount of Ca and Pi in the retentate of the 0.1 micron filtration.

A stabilized-ACP or ACFP complex as referred to herein include a stabilized-ACP or ACFP complex as described in PCT/AU2006/000885 the contents of which are incorporated by reference.

A "superloaded" phosphopeptide or phosphoprotein (PP) stabilized-amorphous calcium phosphate (ACP) or amorphous calcium fluoride phosphate (ACFP) complex. The complex may be formed at any pH (eg 3-10). Preferably the phosphopeptide includes the sequence -A-B-C-, where A is a phosphoamino acid, preferably phosphoserine, B is any amino acid including a phosphoamino acid and C is glutamic acid, aspartic acid or a phosphoamino acid. The phosphoamino acid may be phosphoserine. The PP is superloaded with calcium and phosphate ions. The calcium ions may be in the range 30-1000 mol Ca per mole of PP, or in the range of 30-100 or 30-50 mole Ca per mole of PP. In another embodiment, the mol Ca per mol of PP is at least 25, 30, 35, 40, 45 or 50.

The phosphopeptide or phosphoprotein (PP) stabilized amorphous calcium phosphate or amorphous calcium fluoride phosphate complex may have a calcium ion content greater than about 30 moles of calcium per mole of PP. In a preferred embodiment, the calcium ion content is in the range of about 30 to 100 moles of calcium per mole of PP. More preferably, the calcium ion content is in the range of about 30 to about 50 moles of calcium per mole of PP.

The phosphopeptide or phosphoprotein (PP) stabilized-amorphous calcium phosphate (ACP) or amorphous calcium fluoride phosphate (ACFP) complex may be produced by a method comprising the steps of:
(i) obtaining solutions comprising calcium, inorganic phosphate and fluoride (optional); and
(ii) admixing (i) with a solution comprising PP-ACP.

In a preferred embodiment, the PP is casein phosphopeptide (CPP).

The PP stabilized ACP and/or ACFP complex may further include at least an equal amount by weight of calcium phosphate. Preferably the calcium phosphate is $CaHPO_4$. Preferably, the calcium phosphate (e.g. $CaHPO_4$) is dry blended with the PP stabilized ACP and/or ACFP complex. In a preferred embodiment, the PP-ACP and/or PP-ACFP complex:calcium phosphate ratio is about 1:1-50. more preferably about 1: 1-25, more preferably about 1:5-15. In one embodiment, the PP-ACP and/or PP-ACFP complex: calcium phosphate ratio is about 1:10.

The oral care formulation that includes a phosphopeptide or phosphoprotein (PP) stabilized amorphous calcium phosphate (ACP) and/or amorphous calcium fluoride phosphate (ACFP) complex having a calcium ion content greater than about 30 moles of calcium per mole of PP when used in the oral cavity may be produced by a method including the steps of:
(i) obtaining a powder including a PP-ACP and/or PP-ACFP complex;
(ii) dry blending with an effective amount of calcium phosphate; and
(iii) formulating the dry blended PP-ACP and/or PP-ACFP and calcium phosphate mixture into an oral care formulation.

Preferably, the form of calcium phosphate for dry blending is any soluble calcium phosphate including, but not limited to, $CaHPO_4$, $Ca_2HPO_4$ and calcium lactate.

A composition as described herein may further include free fluoride ions. The fluoride ions may be from any suitable source. A source of fluoride ions may include free fluoride ions or fluoride salts. Examples of sources of fluoride ions include, but are not limited to the following: sodium fluoride, sodium monofluorophosphate, stannous fluoride, sodium silicofluoride and amine fluoride. These may be provided in solution (typically an aqueous solution), or a suspension.

The fluoride ions are preferably present in the composition in an amount greater than 1 ppm. More preferably, the amount is more than 3 ppm. In another embodiment, it is preferably more than 10 ppm. In typical embodiments described below, the amount may be several hundred or thousand ppm. The fluoride content is typically measured as a ppm in oral compositions in the manner commonly used in the art. Where the fluoride is provided from a source with the stabilized ACP, the ppm refers to the concentration of the fluoride in that source, typically a solution or suspension of bioavailable fluoride.

A stannous-associated ACP or ACFP complex as referred to herein include any described in PCT/AU2014/050447, the entire contents of which are incorporated by reference in its entirety.

A composition as described herein for use in a method of use of the invention may include a stannous-associated ACP or ACFP complex. The composition may include 2% CPP-ACP and 290 ppm fluoride with 220 ppm fluoride as stannous fluoride and 70 ppm as sodium fluoride.

"Phosphopeptide" in the context of the description of this invention means an amino acid sequence in which at least one amino acid is phosphorylated. Preferably, the phosphopeptide includes one or more of the amino acid sequence -A-B-C-, where A is a phosphoamino residue, B is any amino acyl residue including a phosphoamino residue and C is selected from a glutamyl, aspartyl or phosphoamino residue. Any of the phosphoamino residues may independently be a phosphoseryl residue. B is desirably a residue the side-chain of which is neither relatively large nor hydrophobic. It may be Gly, Ala, Val, Met, Leu, Ile, Ser, Thr, Cys, Asp, Glu, Asn, Gln or Lys.

In another embodiment, at least two of the phosphoamino acids in the sequence are preferably contiguous. Preferably the phosphopeptide includes the sequence A-B-C-D-E, where A, B, C, D and E are independently phosphoserine, phosphothreonine, phosphotyrosine, phosphohistidine, glutamic acid or aspartic acid, and at least two, preferably three, of the A, B, C, D and E are a phosphoamino acid. In a preferred embodiment, the phosphoamino acid residues are phosphoserine, most preferably three contiguous phosphoserine residues. It is also preferred that D and E are independently glutamic or aspartic acid.

In one embodiment, the ACP or ACFP is stabilized by a casein phosphopeptide (CPP), which is in the form of intact casein or fragment of the casein, and the complex formed preferably has the formula $[CPP(ACP)_8]_n$ or $[(CPP)(ACFP)_8]_n$ where n is equal to or greater than 1, for example 6. The complex formed may be a colloidal complex, where the core particles aggregate to form large (eg 100 nm) colloidal particles suspended in water. Thus, the PP can be a casein protein or a phosphopeptide.

The PP may be from any source; it may be present in the context of a larger polypeptide, including a full length casein polypeptide, or it may be isolated by tryptic or other enzymatic or chemical digestion of casein, or other phosphoamino acid rich proteins such as phosphitin, or by chemical or recombinant synthesis, provided that it comprises the sequence -A-B-C- or A-B-C-D-E as described above. The sequence flanking this core sequence may be any sequence. However, those flanking sequences in $\alpha_{s1}(59-79)$, $\beta(1-25)$, $\alpha_{s2}(46-70)$ and $\alpha_{s2}(1-21)$ are preferred. The flanking sequences may optionally be modified by deletion, addition or conservative substitution of one or more residues. The amino acid composition and sequence of the flanking region are not critical.

Examples of conservative substitutions are shown in Table A below.

TABLE A

| Original Residue | Exemplary Conservative Substitution | Preferred Conservative Substitution |
|---|---|---|
| Ala | Val, Leu, Ile | Val |
| Asn | Gln Lys His Phe | Gln |
| Gln | Asn | Asn |
| Gly | Pro | Pro |
| Ile | Leu, Val, Met, Ala, Phe | Leu |
| Leu | Ile, Val, Met, Ala, Phe | Ile |
| Lys | Arg, Gln, Asn | Arg |
| Phe | Leu, Val, Ile, Ala | Leu |
| Pro | Gly | Gly |
| Ser | Thr | Thr |
| Val | Ile, Leu, Met, Phe, Ala | Leu |
| Asp | Glu | Glu |
| Thr | Ser | Ser |
| Trp | Tyr | Tyr |
| Tyr | Trp Phe Thr Ser | Phe |

The flanking sequences may also include non-naturally occurring amino acid residues. Commonly encountered amino acids which are not encoded by the genetic code, include:
2-amino adipic acid (Aad) for Glu and Asp;
2-aminopimelic acid (Apm) for Glu and Asp;
2-aminobutyric (Abu) acid for Met, Leu, and other aliphatic amino acids;
2-aminoheptanoic acid (Ahe) for Met, Leu and other aliphatic amino acids;
2-aminoisobutyric acid (Aib) for Gly;
cyclohexylalanine (Cha) for Val, and Leu and Ile;
homoarginine (Har) for Arg and Lys;
2, 3-diaminopropionic acid (Dpr) for Lys, Arg and His;
N-ethylglycine (EtGly) for Gly, Pro, and Ala;
N-ethylasparigine (EtAsn) for Asn, and Gln;
Hydroxyllysine (Hyl) for Lys;
allohydroxyllysine (AHyl) for Lys;
3-(and 4) hydroxyproline (3Hyp, 4Hyp) for Pro, Ser, and Thr;
alloisoleucine (AIle) for Ile, Leu, and Val;
ρ-amidinophenylalanine for Ala;
N-methylglycine (MeGly, sarcosine) for Gly, Pro, Ala.
N-methylisoleucine (MeIle) for Ile;
Norvaline (Nva) for Met and other aliphatic amino acids;
Norleucine (Nle) for Met and other aliphatic amino acids;
Ornithine (Orn) for Lys, Arg and His;
Citrulline (Cit) and methionine sulfoxide (MSO) for Thr, Asn and Gln;
N-methylphenylalanine (MePhe), trimethylphenylalanine, halo (F, Cl, Br and I) phenylalanine, triflourylphenylalanine, for Phe.

In one embodiment, the PP is one or more phosphopeptides selected from the group consisting of $\alpha_{s1}(59-79)$ [1], $\beta(1-25)$ [2], $\alpha_{s2}(46-70)$ [3] and $\alpha_{s2}(1-21)$ [4]:

[1]    Gln$^{59}$-Met-Glu-Ala-Glu-Ser(P)-Ile-Ser(P)-Ser(P)-Ser(P)-Glu-Glu-Ile-Val-Pro-Asn-Ser(P)-Val-Glu-Gln-Lys$^{79}$ $\alpha_{s1}(59-79)$

[2]    Arg$^{1}$-Glu-Leu-Glu-Glu-Leu-Asn-Val-Pro-Gly-Glu-Ile-Val-Glu-Ser(P)-Leu-Ser(P)-Ser(P)-Ser(P)-Glu-Glu-Ser-Ile-Thr-Arg$^{25}$ $\beta(1-25)$

[3]    Asn$^{46}$-Ala-Asn-Glu-Glu-Glu-Tyr-Ser-Ile-Gly-Ser(P)-Ser(P)-Ser(P)-Glu-Glu-Ser(P)-Ala-Glu-Val-Ala-Thr-Glu-Glu-Val-Lys$^{70}$ $\alpha_{s2}(46-70)$

[4]    Lys$^{1}$-Asn-Thr-Met-Glu-His-Val-Ser(P)-Ser(P)-Ser(P)-Glu-Glu-Ser-Ile-Ile-Ser(P)-Gln-Glu-Thr-Tyr-Lys$^{21}$ $\alpha_{s2}(1-21)$.

In another embodiment of the invention, the stabilized ACP and/or stabilized ACFP complex is incorporated into oral compositions such as toothpaste, mouth washes or formulations for the mouth to aid in the prevention and/or treatment of gingivitis or periodontitis. The oral compositions comprising an amount of stabilized ACP and/or ACFP sufficient to form a layer on a dental surface, preferably, the layer has a calcium:phosphate ratio equivalent to normal apatite, for example the ratio is about 2:1. The layer may contain an amount of calcium that is about 20 wt %. The stabilized ACP and/or ACFP complexes may comprise 0.01 to 50% by weight of the composition, preferably 1.0 to 50%, preferably 1.0 to 30%, preferably 1.0 to 20%, preferably 1.0 to 10%, preferably 2 to 10% by weight of the composition. In a particularly preferred embodiment, the oral composition of the present invention contains about 2% stabilized ACP or ACFP complexes or a mixture of both. The oral composition of this invention which contains the above-mentioned agents may be prepared and used in various forms applicable to the mouth such as dentifrice including toothpastes, toothpowders and liquid dentifrices, mouthwashes, mouthrinses, mouth sprays, varnish, dental cement, troches, chewing gums, dental pastes, gingival massage creams, gargle tablets, dairy products and other foodstuffs. The oral composition according to this invention may further include additional well known ingredients depending on the type and form of a particular oral composition. Certain compositions of the invention such as toothpastes, toothpowders and liquid dentifrices, mouthwashes, mouthrinses and mouth sprays have relatively low viscosity and have a positive effect on treatment or prevention without significant residence time in the oral cavity.

In certain preferred forms of the invention an oral composition may be substantially liquid in character, such as a mouthwash, rinse or spray. In such a preparation the vehicle is typically a water-alcohol mixture desirably including a humectant as described below. Generally, the weight ratio of water to alcohol is in the range of from about 1:1 to about 20:1. The total amount of water-alcohol mixture in this type of preparation is typically in the range of from about 70 to about 99.9% by weight of the preparation. The alcohol is typically ethanol or isopropanol. Ethanol is preferred.

In other desirable forms of this invention, the composition may be substantially solid or pasty in character, such as toothpowder, a dental tablet or a toothpaste (dental cream) or a gel dentifrice. The vehicle of such solid or pasty oral preparations generally contains dentally acceptable polishing material. Examples of polishing materials are water-insoluble sodium metaphosphate, potassium metaphosphate, tricalcium phosphate, dihydrated calcium phosphate, anhydrous dicalcium phosphate, calcium pyrophosphate, magnesium orthophosphate, trimagnesium phosphate, calcium carbonate, hydrated alumina, calcined alumina, aluminium silicate, zirconium silicate, silica, bentonite, and mixtures thereof. Other suitable polishing material include the particulate thermosetting resins such as melamine-, phenolic, and urea-formaldehydes, and cross-linked polyepoxides and polyesters. Preferred polishing materials include crystalline silica having particle sizes of up to about 5 microns, a mean particle size of up to about 1.1 microns, and a surface area of up to about 50,000 $cm^2/g$., silica gel or colloidal silica, and complex amorphous alkali metal aluminosilicate.

When visually clear gels are employed, a polishing agent of colloidal silica, such as those sold under the trademark SYLOID as Syloid 72 and Syloid 74 or under the trademark SANTOCEL as Santocel 100, alkali metal aluminosilicate complexes are particularly useful since they have refractive indices close to the refractive indices of gelling agent-liquid (including water and/or humectant) systems commonly used in dentifrices.

Many of the so-called "water insoluble" polishing materials are anionic in character and also include small amounts of soluble material. Thus, insoluble sodium metaphosphate may be formed in any suitable manner, for example as illustrated by Thorpe's Dictionary of Applied Chemistry, Volume 9, 4th Edition, pp. 510-511. The forms of insoluble sodium metaphosphate known as Madrell's salt and Kurrol's salt are further examples of suitable materials. These metaphosphate salts exhibit only a minute solubility in water, and therefore are commonly referred to as insoluble metaphosphates (IMP). There is present therein a minor amount of soluble phosphate material as impurities, usually a few percent such as up to 4% by weight. The amount of soluble phosphate material, which is believed to include a soluble sodium trimetaphosphate in the case of insoluble metaphosphate, may be reduced or eliminated by washing with water if desired. The insoluble alkali metal metaphosphate is typically employed in powder form of a particle size such that no more than 1% of the material is larger than 37 microns.

The polishing material is generally present in the solid or pasty compositions in weight concentrations of about 10% to about 99%. Preferably, it is present in amounts from about 10% to about 75% in toothpaste, and from about 70% to about 99% in toothpowder. In toothpastes, when the polishing material is silicious in nature, it is generally present in an amount of about 10-30% by weight. Other polishing materials are typically present in amount of about 30-75% by weight.

In a toothpaste, the liquid vehicle may comprise water and humectant typically in an amount ranging from about 10% to about 80% by weight of the preparation. Glycerine, propylene glycol, sorbitol and polypropylene glycol exemplify suitable humectants/carriers. Also advantageous are liquid mixtures of water, glycerine and sorbitol. In clear gels where the refractive index is an important consideration, about 2.5-30% w/w of water, 0 to about 70% w/w of glycerine and about 20-80% w/w of sorbitol are preferably employed.

Toothpaste, creams and gels typically contain a natural or synthetic thickener or gelling agent in proportions of about 0.1 to about 10, preferably about 0.5 to about 5% w/w. A suitable thickener is synthetic hectorite, a synthetic colloidal magnesium alkali metal silicate complex clay available for example as Laponite (e.g. CP, SP 2002, D) marketed by Laporte Industries Limited. Laponite D is, approximately by weight 58.00% $SiO_2$, 25.40% MgO, 3.05% $Na_2O$, 0.98% $Li_2O$, and some water and trace metals. Its true specific gravity is 2.53 and it has an apparent bulk density of 1.0 g/ml at 8% moisture.

Other suitable thickeners include Irish moss, iota carrageenan, gum tragacanth, starch, polyvinylpyrrolidone, hydroxyethylpropylcellulose, hydroxybutyl methyl cellulose, hydroxypropyl methyl cellulose, hydroxyethyl cellulose (e.g. available as Natrosol), sodium carboxymethyl cellulose, and colloidal silica such as finely ground Syloid (e.g. 244). Solubilizing agents may also be included such as humectant polyols such propylene glycol, dipropylene glycol and hexylene glycol, cellosolves such as methyl cellosolve and ethyl cellosolve, vegetable oils and waxes containing at least about 12 carbons in a straight chain such as olive oil, castor oil and petrolatum and esters such as amyl acetate, ethyl acetate and benzyl benzoate.

It will be understood that, as is conventional, the oral preparations will usually be sold or otherwise distributed in suitable labelled packages. Thus, a jar of mouth rinse will have a label describing it, in substance, as a mouth rinse or mouthwash and having directions for its use; and a toothpaste, cream or gel will usually be in a collapsible tube, typically aluminium, lined lead or plastic, or other squeeze, pump or pressurized dispenser for metering out the contents, having a label describing it, in substance, as a toothpaste, gel or dental cream.

Organic surface-active agents may be used in the compositions of the present invention to achieve increased prophylactic action, assist in achieving thorough and complete dispersion of the active agent throughout the oral cavity, and render the instant compositions more cosmetically acceptable. The organic surface-active material is preferably anionic, non-ionic or ampholytic in nature and preferably does not interact with the active agent. It is preferred to employ as the surface-active agent a detersive material which imparts to the composition detersive and foaming properties. Suitable examples of anionic surfactants are water-soluble salts of higher fatty acid monoglyceride monosulfates, such as the sodium salt of the monosulfated monoglyceride of hydrogenated coconut oil fatty acids, higher alkyl sulfates such as sodium lauryl sulfate, alkyl aryl sulfonates such as sodium dodecyl benzene sulfonate, higher alkylsulfo-acetates, higher fatty acid esters of 1,2-dihydroxy propane sulfonate, and the substantially saturated higher aliphatic acyl amides of lower aliphatic amino carboxylic acid compounds, such as those having 12 to 16 carbons in the fatty acid, alkyl or acyl radicals, and the like. Examples of the last mentioned amides are N-lauroyl sarcosine, and the sodium, potassium, and ethanolamine salts of N-lauroyl, N-myristoyl, or N-palmitoyl sarcosine which should be substantially free from soap or similar higher fatty acid material. The use of these sarconite compounds in the oral compositions of the present invention is particularly advantageous since these materials exhibit a prolonged marked effect in the inhibition of acid formation in the oral cavity due to carbohydrates breakdown in addition to exerting some reduction in the solubility of tooth enamel in acid solutions. Examples of water-soluble non-ionic surfactants suitable for use are condensation products of ethylene oxide with various reactive hydrogen-containing compounds reactive therewith having long hydrophobic chains (e.g. aliphatic chains of about 12 to 20 carbon atoms), which condensation products ("ethoxamers") contain hydrophilic polyoxyethylene moieties, such as condensation products of poly (ethylene oxide) with fatty acids, fatty alcohols, fatty amides, polyhydric alcohols (e.g. sorbitan monostearate) and polypropyleneoxide (e.g. Pluronic materials).

The surface active agent is typically present in amount of about 0.1-5% by weight. It is noteworthy, that the surface active agent may assist in the dissolving of the active agent of the invention and thereby diminish the amount of solubilizing humectant needed.

Various other materials may be incorporated in the oral preparations of this invention such as whitening agents, preservatives, silicones, chlorophyll compounds and/or ammoniated material such as urea, diammonium phosphate, and mixtures thereof. These adjuvants, where present, are incorporated in the preparations in amounts which do not substantially adversely affect the properties and characteristics desired.

Any suitable flavouring or sweetening material may also be employed. Examples of suitable flavouring constituents are flavouring oils, e.g. oil of spearmint, peppermint, wintergreen, sassafras, clove, sage, eucalyptus, marjoram, cinnamon, lemon, and orange, and methyl salicylate. Suitable sweetening agents include sucrose, lactose, maltose, sorbitol, xylitol, sodium cyclamate, perillartine, AMP (aspartyl phenyl alanine, methyl ester), saccharine, and the like. Suitably, flavour and sweetening agents may each or together comprise from about 0.1% to 5% more of the preparation.

The compositions of this invention can also be incorporated in lozenges, or in chewing gum or other products, e.g. by stirring into a warm gum base or coating the outer surface of a gum base, illustrative of which are jelutong, rubber latex, vinylite resins, etc., desirably with conventional plasticizers or softeners, sugar or other sweeteners or such as glucose, sorbitol and the like. The composition of the invention may be a dual phase composition wherein each phase permits release of components over different time periods.

An alternative composition may be one that provides stabilized ACP or ACFP and a stannous compound that then in situ, such as the oral cavity, forms stannous-associated stabilized ACP or ACFP. An exemplary composition may be a chewing gum that contains stabilized ACP or ACFP in the pellet and a stannous compound in the centre chew.

In a further aspect, the invention provides compositions including pharmaceutical compositions comprising stabilized ACP or ACFP complexes as described above together with a compound capable of increasing or maintaining the pH of a solution and a pharmaceutically-acceptable carrier. Such compositions may be selected from the group consisting of dental, anticariogenic compositions and therapeutic compositions. Dental compositions or therapeutic compositions may be in the form of a gel, liquid, solid, powder, cream or lozenge. Therapeutic compositions may also be in the form of tablets or capsules. In one embodiment, the stabilized ACP or ACFP complexes are substantially the only active components of such a composition. For example, a crème formulation may be employed containing:water; glycerol; CPP-ACP/$SnF_2$; D-sorbitol; silicon dioxide; sodium carboxymethylcellulose (CMC-Na); propylene glycol; titanium dioxide; xylitol; phosphoric acid; guar gum; sodium saccharin; ethyl p-hydroxybenzoate; magnesium oxide; butyl p-hydroxybenzoate and propyl p-hydroxybenzoate.

The invention further includes a formulation described above provided together with instructions for its use to treat or prevent any one or more of dental caries or tooth decay, dental erosion and fluorosis, dentinal hypersensitivity, dental plaque, gingivitis or periodontitis.

In another embodiment, the compositions of the invention as described herein do not include a phosphate buffer and/or a calcium chelator. For example, any dentifrice described herein may not include a phosphate buffer and/or a calcium chelator.

In an embodiment of the present invention there is provided a composition, wherein the composition does not include a phosphate buffer and/or calcium chelator.

In another embodiment, the compositions of the invention as described herein do not include a viscosity regulator, or a viscosity regulator at 0.5 to 50%.

In another embodiment, the compositions of the invention as described herein do not include sodium carboxymethylcellulose, or 0.01 to 10% sodium carboxymethylcellulose having the esterification degree of 0.7 to 1.0.

In one embodiment, the active components of the composition consist essentially of the stabilized ACP or ACFP complexes.

It will be clearly understood that, although this specification refers specifically to applications in humans, the invention is also useful for veterinary purposes. Thus in all aspects the invention is useful for domestic animals such as cattle, sheep, horses and poultry; for companion animals such as cats and dogs; and for zoo animals.

One example of a mineralizing composition comprises the following (in decreasing order of proportion):
water
glycerol
CPP-ACP/$SnF_2$
D-sorbitol
silicon dioxide
sodium carboxymethylcellulose (CMC-Na)
propylene glycol
titanium dioxide
xylitol
phosphoric acid
guar gum
sodium saccharin
ethyl p-hydroxybenzoate magnesium oxide
butyl p-hydroxybenzoate
propyl p-hydroxybenzoate.

The invention also provides a kit comprising stabilized amorphous calcium phosphate (ACP) and/or stabilized amorphous calcium fluoride phosphate (ACFP) said kit being adapted for use in the above described methods.

The kit may include:
- a container holding a composition comprising stabilized amorphous calcium phosphate (ACP) and/or stabilized amorphous calcium fluoride phosphate (ACFP);
- a label or package insert with instructions for use.

In certain embodiments the kit may contain one or more further active principles or ingredients for treatment of a disease or condition.

The kit may comprise a container and a label or package insert on or associated with the container. Suitable containers include, for example, bottles, vials, syringes, blister pack, etc. The containers may be formed from a variety of materials such as glass or plastic. The container holds a therapeutic composition which is effective for treating the condition and may have a sterile access port (for example the container may be an intravenous solution bag or a vial having a stopper pierceable by a hypodermic injection needle). The label or package insert indicates that the therapeutic composition is used for treating the condition of choice. In one embodiment, the label or package insert includes instructions for use and indicates that the therapeutic composition can be used for treatment of the given disease or condition.

The kit may comprise (a) a therapeutic composition; and (b) a second container with a second active principle or ingredient contained therein. The kit in this embodiment of the invention may further comprise a package insert indicating that the composition and other active principle can be used to treat a disorder or condition as described herein or prevent a complication stemming from dybiosis. Alternatively, or additionally, the kit may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

The invention will now be further described with reference to the following non-limiting examples.

EXAMPLES

Example 1

Clinical Study: Prebiotic Effect of CPP-ACP on Supragingival Dental Plaque and Oral Health Study Objectives Primary Objective To compare the effect of chewing a sugar-free gum containing 56.4 mg CPP-ACP, chewing a sugar-free gum containing 18.8 mg CPP-ACP, and no gum chewing, each in conjunction with normal oral hygiene procedures over 14 days, on the microbial composition of supragingival plaque formed on the maxillary molars.

Secondary Objectives

A. To compare the effect of chewing a sugar-free gum containing 56.4 mg CPP-ACP, chewing a sugar-free gum containing 18.8 mg CPP-ACP, and no gum chewing, each in conjunction with normal oral hygiene procedures over 14 days, on development of supragingival plaque.

B. To compare the effect of chewing a sugar-free gum containing 56.4 mg CPP-ACP, chewing a sugar-free gum containing 18.8 mg CPP-ACP, and no gum chewing, each in conjunction with normal oral hygiene procedures over 14 days, on development of gingivitis.

Human Ethics Approval

Human ethics approval was obtained from the University of Melbourne Human Research Ethics Committee before commencing the study. All participants were required to provide written informed consent before commencing the study.

Study Plan

Study Design

This examiner-blinded, randomized controlled clinical trial used a three-treatment, three-period cross-over design to assess the effects of chewing with a sugar-free gum containing 56.4 mg CPP-ACP, chewing with sugar-free gum containing 18.8 mg CPP-ACP, and no gum chewing over 14 days on the development and change in composition of supragingival dental plaque as well as development of gingivitis in the presence of normal oral hygiene procedures. Participants were randomly assigned to one of three treatments with each treatment period comprising 14 days. The three treatments were as follows:

A. chewing sugar-free gum containing 56.4 mg CPP-ACP for 20 minutes, six times per day, for 14 consecutive days;

B. chewing sugar-free gum containing 18.8 mg CPP-ACP for 20 minutes, six times a day, for 14 consecutive days;

C. no gum chewing.

During the treatment period, each subject continued with oral hygiene practices consisting of brushing twice a day with a fluoride toothpaste (supplied) and tooth brush (supplied). Participants chewing the gum products were requested not to consume antimicrobial mints, lozenges, films and other non-study chewing gums during the treatment period. Similarly, participants not chewing gum during the treatment period were requested not to consume antimicrobial mints, lozenges, films and other non-study chewing gums during the treatment period.

Source of Participants

Participants were recruited from the staff of the Melbourne Dental School and the Melbourne Dental Clinic at the University of Melbourne. All study participants provided signed informed consent prior to participation.

Participant Selection Criteria

Inclusion Criteria:

To be eligible to participate in this study, an individual met ALL of the following criteria:

1. Ability to understand, and willingness and ability to read and sign, the informed consent form.
2. Age range: 18 to 55 years old.
3. Good general health.
4. Minimum of 20 natural teeth.
5. A gum-stimulated whole salivary flow rate≥1.0 ml/minute and unstimulated whole salivary flow rate≥0.2 ml/minute.
6. Willingness to comply with all study procedures and be available for the duration of the study.

Exclusion Criteria:

Individuals who manifest ANY of the following exclusion criteria at the time of randomization were not eligible for the study:

1. Allergy to milk protein or other ingredients in the gum product.
2. Orthodontic appliances or removable prostheses.
3. Veneers, or more than one incisor with a prosthetic crown.
4. Gross oral pathology (including periodontal disease (CPITN≥3) and tumours of the soft or hard oral tissues).
5. Chronic disease with concomitant oral manifestations (e.g., diabetes [irrespective of level of control], human immunodeficiency virus infection or acquired immunodeficiency syndrome, use of medications associated with gingival hyperplasia).
6. Unrestored dentinal caries.
7. Treatment with antibiotics or anti-inflammatory medication in the month prior to starting the study.
8. Concomitant pharmacotherapy with drugs that may interact with test drug.
9. History of conditions requiring antibiotic coverage prior to invasive dental procedures.
10. Pregnancy/lactation.

Test Products
Description of Test Products
Each participant was randomly allocated to one of the following three treatments:
A. Sugar-free chewing gum containing 56.4 mg CPP-ACP for 20 minutes, six times per day, for 14 consecutive days;
B. Sugar-free chewing gum containing 18.8 mg CPP-ACP for 20 minutes, six times a day, for 1 consecutive days;
C. no gum chewing.

Method of Dispensing
At the beginning of each leg, participants were issued with a package containing their allocated treatment for that period, a tube of fluoride toothpaste and a toothbrush. Participants returned any unused gum and all used gum wrappers when they attended for the 14-day assessment at the end of each treatment period. The quantities of gums dispensed and returned were recorded.

Method and Timing of Administration
When allocated a gum test product, participants chewed their allocated gum for 20 minutes, six times per day for 14 consecutive days at the following times: after breakfast, after morning tea, after lunch, after afternoon tea, after dinner and before retiring.

Methods of Randomization and Blinding
A block randomization schedule was generated which ensured that all six treatment combinations (ABC, ACB, BAC, BCA, CAB, CBA) are equally likely.

The study was examiner-blinded. Throughout the study, the clinical examiner and the laboratory staff processing the plaque samples were unaware of which treatment arm a participant had been allocated. The participants and study personnel were also unaware of which chewing gum has been allocated, as the chewing gums were provided in identical coded packages. As participants did not chew gum in one treatment period, it was impossible to fully blind the participants to treatment allocation. Personnel dispensing the test material or supervising their use did not participate in the examination of the participants or analysis of plaque samples in order to minimize potential bias.

A researcher not involved in any of the analysis kept a master list of the code identification.

Assignment of Participants to Treatment:
Following the baseline examination, participants were assigned a participant number. Participants were randomly assigned to one of the three treatments. Randomization was determined from a standard randomisation table for the number of treatments in the parallel study.

Duration of Treatment
Each of the three treatment periods were for 14 consecutive days. The treatment periods were separated by 14-day washout periods.

Concomitant Procedures
Participants were instructed to continue to brush their teeth with the supplied fluoride toothpaste and toothbrush twice a day. Participants were instructed to abstain from mouth rinsing (except with water); flossing; using other oral hygiene aids; consuming antimicrobial mints, lozenges, films and other non-study chewing gum during each 14-day treatment period.

Measurements and Observations
Efficacy Endpoints
Clinical Examinations
At the start and finish of the treatment period, participants had an examination for gingivitis and plaque, and supragingival plaque was collected from the buccal surfaces of the maxillary molars. Following the completion of the examination and supragingival plaque collection, participants received a supragingival scaling, clean and prophylaxis of all their teeth. At the completion of the last examination for leg 3, each participant received a professional fluoride treatment.

Measurement of Plaque and Gingivitis
Supragingival plaque was assessed using the Turesky modification of the Quigley-Hein Index (Turesky et al 1970 J Periodontol 41(1):41-43). This index is recognised as a reliable estimate of the tooth area covered by plaque and is frequently used for evaluating anti-plaque agents. The plaque index was obtained by adding the scores for each tooth and dividing by the number of surfaces examined. Plaque scores associated with unrestored labial, buccal and lingual surfaces of all teeth, except third molars were assessed. Each surface was assigned a score from 0 to 5.

Gingivitis was measured using the Modified Gingival Index [Lobene et al 1986]. This index is a modification of the Loe and Silness Gingival Index and allows greater discrimination for mild and moderate gingivitis. In this study, gingival inflammation on a scale from 0 to 4 was scored for gingival tissues associated with four sites (buccal, lingual, mesial and distal) of all teeth.

Supragingival Plaque Collection
Participants had all supragingival plaque collected from the buccal surfaces of their maxillary molars (teeth 17, 16, 26 & 27) with a sterile scaling instrument. The plaque samples from each tooth were placed in separate sterile tubes, to give four samples per participant.

A one-part label was affixed to each container of plaque collected from each participant. The label contained the following information:
participant number
treatment code (A, B or C)
tooth (17, 16, 26 or 27)
treatment period (Leg 1, Leg 2 or Leg 3)
time (0 or 14 days).

Plaque mass for each of the four samples from each participant was recorded to allow standardisation of DNA extraction procedures (0.2 mg per sample required for DNA extraction). Homogenised plaque samples were stored at −80° C. until required.

Plaque Microbial Analysis
Genomic DNA was extracted from the plaque using a combination of mechanical disruption of the cells via a Precellys homogeniser and the chemical extraction and purification of the genomic DNA via the PowerLyzer PowerSoil DNA Isolation Kit (MoBio). Quantitation of the extracted DNA was achieved using a Qubit dsDNA High Sensitivity Assay kit (ThermoFisher), before 5 ng DNA was used as template in a PCR reaction that amplified the V4 variable region of the 16S ribosomal RNA gene and individually barcoded the PCR product from each sample. The barcoded DNA was then sequenced using an Ion Torrent Personal Genome machine and Torrent Suite™ Software (ThermoFisher).

Analysis of the resulting sequence of the 16S ribosomal RNA gene enabled identification of the bacterial population present in each sample, down to the species level. The BAM files produced with Torrent Suite™ Software were transferred from the Ion Torrent to the local Ion Reporter server, where the Ion Reporter Software 16S metagenomics workflow was used to identify, at the genus or species level, the microbes present in the complex polybacterial samples, using both the premium curated MicroSEQ™ ID 16S rRNA reference database and the curated Greengenes database. The data were collated in Microsoft Excel.

Statistical Methods

Sample Size Determination

Table 1 below shows the estimated sample sizes for each group for mean differences in abundance of *S. sanguinis* of 1.5%, 2.0%, 2.5%, and 3.0%, standard deviations ranging from 3.5% to 5.5%, and the power of the test at 80%. It assumes a two-tailed paired t-test and $\alpha=0.05$. The range of means and standard deviations used in the sample size calculations was based on a previous pilot study.

TABLE 1

Estimated Sample Size per Treatment Group

| Difference in Means | Standard Deviation | | | | | |
|---|---|---|---|---|---|---|
| | 3.0 | 3.5 | 4.0 | 4.5 | 5.0 | 5.5 |
| 1.5 | 34 | 45 | 58 | 73 | 90 | 108 |
| 2.0 | 20 | 27 | 34 | 42 | 52 | 62 |
| 2.5 | 14 | 18 | 23 | 28 | 34 | 40 |
| 3.0 | 10 | 13 | 16 | 20 | 24 | 29 |
| 3.5 | 8 | 10 | 13 | 16 | 19 | 22 |

Table 2 Table 2 shows the estimated size for each group allowing for a 10% percent attrition rate during the study follow-up period.

TABLE 2

Estimated Sample Size per Treatment Group

| Difference in Means | Standard Deviation | | | | | |
|---|---|---|---|---|---|---|
| | 3.0 | 3.5 | 4.0 | 4.5 | 5.0 | 5.5 |
| 1.5 | 38 | 50 | 64 | 81 | 100 | 120 |
| 2.0 | 22 | 30 | 38 | 47 | 58 | 69 |
| 2.5 | 16 | 20 | 26 | 31 | 38 | 44 |
| 3.0 | 11 | 14 | 18 | 22 | 27 | 32 |
| 3.5 | 9 | 11 | 14 | 18 | 21 | 24 |

Assuming a standard deviation of 4.5% and a 10% percent attrition rate, a sample of 18 participants were recruited to allow for a mean difference in abundance of *S. sanguinis* of 3.5% to be detected with a power of 80 percent.

Statistical General Considerations

Randomization and Blinding

The two chewing gums were provided in identical packaging except that each was labelled with a code. The individual pieces of chewing gums were of similar appearance. The code was not released until all statistical analyses had been completed.

Assignment of ID to participants occurred sequentially after each participant had fulfilled the entry criteria.

The study was examiner-blinded. Throughout the study, the dental examiner and the laboratory staff processing the plaque samples were unaware of which treatment arm a participant had been allocated. The participants and study personnel were also unaware of which chewing gum had been allocated, as the chewing gums were provided in identical coded packages. As participants did not chew gum in one treatment period, it was impossible to fully blind the participants to treatment allocation. All participants completed the study.

Compliance Criteria:

Compliance was judged by reviewing participant diaries of product use and recording of remaining clinical supplies.

Statistical Analysis of Demography and Baseline Characteristics

The primary analysis set were all participants who completed the trial without significant protocol violations.

Descriptive statistics (mean, standard deviation and range) were calculated for all continuous variables and frequencies for all ordinal variables. All statistical tests were two-sided and employed a significance level of $\alpha=0.05$. All analyses were performed using the statistical package Stata (StataCorp LP, College Station, Tex., USA) statistical software.

Statistical Analysis of Efficacy Data

The individual 16S rDNA sequences produced for each sample were used to both classify the microbial lineages present (grouped as species level taxa) and determine the abundances of each taxon. Differences in the bacterial community over time was determined by measuring the changes in the relative taxon abundances for each individual.

This enabled a comparison of the effect of CPP-ACP on the bacterial composition of the plaque. The four samples from each individual enabled the determination of intra-subject variation in bacterial composition of plaque.

Results

All subjects completed the study and were deemed to be compliant with the protocol. No adverse events were reported. The treatment with CPP-ACP did not produce a significant change in plaque index of the participants (FIG. 1). Although the CPP-ACP did not affect the plaque index it did have a significant effect on bacterial composition demonstrating a substantial prebiotic effect by promoting the proportions of commensal/beneficial symbionts.

Figure 2:
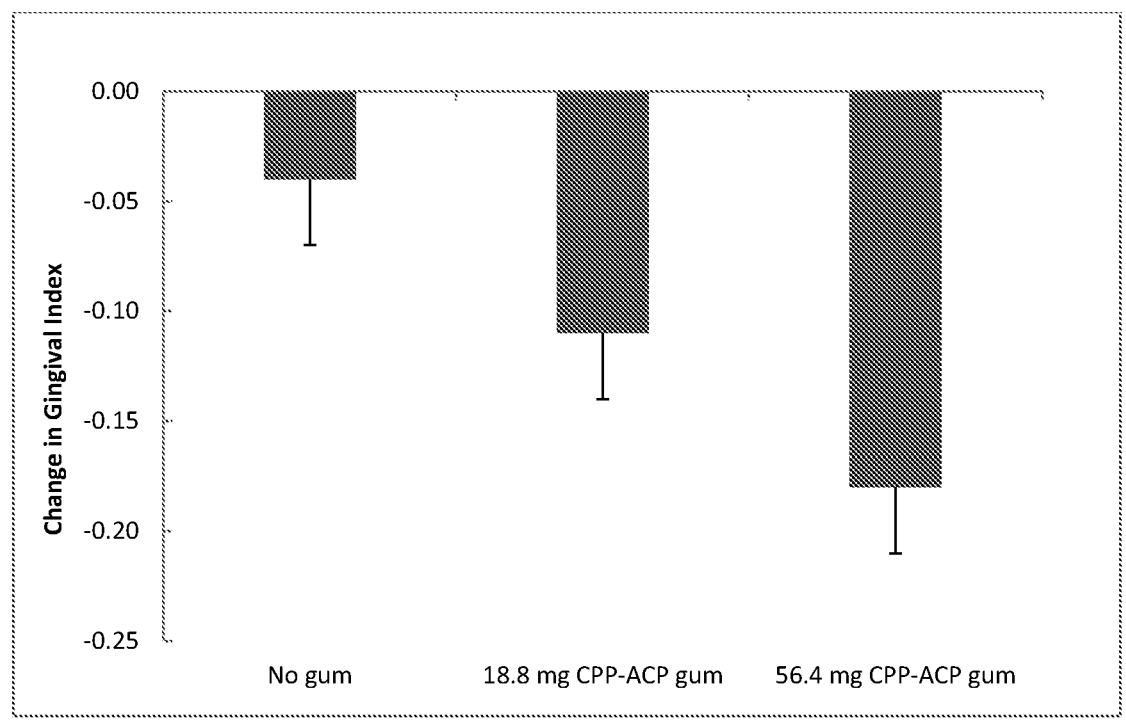
FIG. 2. Effect of CPP-ACP on gingival index in a randomised, controlled clinical trial.

In total, over 300 different bacterial taxa were identified from 54 samples. When the bacterial composition of the supragingival plaque was examined across the treatment groups, it was clear that there were significant changes when the CPP-ACP treatment legs were compared to no treatment. The 18.8 mg CPP-ACP produced statistically significant increases in the proportions of the following bacterial taxa: *Corynebacterium durum* (80% increase); *Rothia dentocariosa* (127% increase); *Streptococcus mitis* (55% increase) and *Streptococcus sanguinis* (112% increase) (Table 3). All of these species are now considered beneficial symbionts as they possess one or both of enzymes systems [Arginine Deiminase and/or Nitrate Reductase] which are known to be beneficial to the host. These significant increases in commensal/beneficial species was CPP-ACP dose-related as the increases were significantly greater for the 56.4 mg CPP-ACP dose. The increases in beneficial species was associated with a concomitant reduction in the proportion of pathogenic species (pathobionts). This increase in the abundances of beneficial symbionts was also reflected in an increase in gingival health as demonstrated by a significant CPP-ACP dose-related improvement in gingival index (FIG. 2).

TABLE 3

Oral species significantly increased by 18.8 mg CPP-ACP are Gram-positive commensals possessing one or both of Arginine Deiminase and Nitrate Reductase systems which promote homeostasis

| Genus | Species | Arginine Deiminase | Nitrate Reductase | % increase in relative abundance |
|---|---|---|---|---|
| Corynebacterium | durum | Yes (partial) | Yes | 80% (p < 0.001) |
| Rothia | dentocariosa | No | Yes | 127% (p < 0.001) |
| Streptococcus | gordonii/mitis | Yes | No | 55% (p < 0.05) |
| Streptococcus | sanguinis | Yes | No | 112% (p < 0.01) |

TABLE 4

Oral species significantly reduced by 18.8 mg CPP-ACP are Gram-negative, inflammogenic anaerobes associated with dysbiosis

| Genus | Species | Arginine Deiminase | Nitrate Reductase | % decrease in relative abundance |
|---|---|---|---|---|
| Leptotrichia | wadei | No | No | 91% (p < 0.001) |
| Leptotrichia | shahii | No | No | 73% (p < 0.01) |
| Leptotrichia | buccalis | No | No | 76% (p < 0.05) |
| Lautropia | mirabilis | No | Yes | 70% (p < 0.05) |

In conclusion this randomised, controlled clinical study demonstrated that CPP-ACP treatment resulted in a significant increase in the proportion of the health-associated symbionts and improvement in oral health indicating that CPP-ACP was a prebiotic.

Example 2

$SnF_2$ Promotes CPP-ACP Prebiosis in a Polymicrobial Model

Multispecies Oral Biofilms Culture

To model supragingival plaque six representative oral bacterial species, *Streptococcus sanguinis* (NCTC 7863), *Streptococcus mutans* Ingbritt, *Actinomyces naeslundii* (NCTC 10301), *Veillonella parvula* (ATCC 17745), *Lactobacillus casei* (NCDO 161) and *Fusobacterium nucleatum* (ATCC 10953) (Table 5) were cultured as a polymicrobial biofilm on a human enamel substratum in a constant-depth film fermenter (CDFF; Cardiff University, UK). The CDFF was housed in a 37° C. incubator under anaerobic conditions which were maintained by a constant flow of 5% $CO_2$ in $N_2$ at 1 L/h. The CDFF contained 15 removable polytetrafluoroethylene (PTFE) pans on a circular platform that was rotated at a constant speed of three rpm. The biofilms were grown on three enamel blocks (see below) in each PTFE pan using an artificial saliva medium (ASM, 2.5 g/L mucin type II (porcine, gastric, Sigma), 2.0 g/L bacteriological peptone (Oxoid), 2.0 g/L tryptone (Oxoid), 1.0 g/L yeast extract (Oxoid), 0.35 g/L NaCl, 0.2 g/L KCl, 0.2 mg/L vitamin K, 1 mg/L haemin and 0.1 g/L cysteine hydrochloride) at a constant flow rate of 30 mL/h. Prior to inoculation, the CDFF pan surfaces were conditioned for 24 h with ASM at a flow rate of 10 mL/h (McBain et al (2003) J Appl Microbiol. 94(4):655-66). In order to mimic in vivo bacterial growth conditions in the oral cavity with dietary sugar intake and to provide a high cariogenic challenge, a 1% (w/v) sucrose solution in ASM was pumped into the CDFF four times a day at four hourly intervals with a flow rate of 30 mL/h for 10 min.

TABLE 5

Bacterial strains used in this study, 16S rRNA gene copy number and species composition of the inocula.

| Bacterial strain[a] | Genome size (bp) | 16S rRNA gene copy number[b] | Number of cells in inoculum ($\times 10^7$)[c] |
|---|---|---|---|
| *Actinomyces naeslundii* NCTC 10301 | 3,091,654 | 2 | 9.90 ± 8.32 |
| *Fusobacterium nucleatum* ssp. polymorphum ATCC 10953 | 2,428,298 | 5 | 11.5 ± 8.79 |
| *Lactobacillus casei* (NCDO 161) | 2,851,896 | 5 | 5.10 ± 2.40 |
| *Streptococcus mutans* (Ingbritt) | 2,030,511 | 5 | 13.7 ± 5.77 |
| *Streptococcus sanguinis* (NCTC 7863) ATCC 10556 | 2,303,750 | 5 | 21.7 ± 10.9 |
| *Veillonella parvula* ATCC 17745 | 2,163,473 | 4 | 5.44 ± 3.08 |

[a] all strains were sourced from the Oral Health Cooperative Research Centre at the Melbourne Dental School
[b] 16S rRNA gene copy number was determined by sequence analysis of the genomes conducted in our laboratory, data not shown.
[c] mean and standard deviation of the number of cells of the inocula used in this study as determined by qPCR.

Three treatments were applied to the polymicrobial biofilms: 290 ppm fluoride with 220 ppm fluoride as $SnF_2$ and 70 ppm fluoride as NaF (referred to as $SnF_2$), 2% CPP-ACP and 2% CPP-ACP-$SnF_2$. These treatments were compared with the control in which the test solution was replaced with ASM. Each treatment was applied using two 10 min pulses of the test solution in ASM with a flow rate of 30 mL/h. The first pulse started 30 min prior to the first sucrose pulse of the morning and the second started 3 h 30 min after the final sucrose pulse of the day.

On day 6, 12 and 19 after inoculation four pans were removed aseptically from the CDFF and replaced with blank sterile pans. Enamel blocks from the pans were removed for bacterial enumeration and transverse microradiography.

Enamel Block Preparation

Three hundred and sixty extracted human third molars were obtained under University of Melbourne ethics approval (HREC #1237616) and sterilized by exposure to 4.1 kGy of gamma radiation. Enamel blocks were cut from the teeth with approximately 6×3×3 mm dimensions using a water-cooled diamond blade saw (Minitom, Struers) and polished using a RotoPol/RotoForce lapping instrument with 1200, 2400, 4000 grit lapping papers (Struers) and 3 and 1 μm diamond polishing pastes (Struers). The blocks were positioned in custom made CDFF pans at a depth of 100 μm and sealed in place with yellow sticky wax (Kemdent) and sterilized by exposure to 4.1 kGy of gamma radiation.

Sampling

Planktonic and loosely attached bacterial cells were firstly removed from the enamel blocks by light washing with 100 µL ASM. To harvest the biofilm cells on each block, the surface was scraped with a sterile scraper with 1 mL of ASM. The biofilm bacterial cells were sedimented by centrifugation (10,000 g, 10 min), the supernatant carefully decanted and the cell pellets stored at −80° C. until required for DNA extraction. The enamel blocks were then used for sectioning and microradiography.

DNA Extraction and Sequencing of Biofilm Samples

For each timepoint, DNA was extracted separately from 8-9 enamel blocks using PowerLyzer® PowerSoil® DNA Isolation Kits (MoBio Laboratories) following the manufacturers "Vacuum Protocol" with a Precellys® bead homogeniser (Bertin Technologies). Samples were quantified using a Qubit™ dsDNA HS assay kit (Life Technologies) before being stored at −80° C.

The Ion Amplicon Library Preparation Fusion Method (Thermo Fisher Scientific), was adapted for amplification of the V4 region of the 16S rRNA gene. PCRs were performed in a 50 µL reaction volume containing 5 ng of DNA, 1× Q5 reaction buffer, 0.3 µM PAGE-purified custom barcoded primers (Thermo Fisher Scientific), 0.2 mM dNTPs and 1 unit of Q5 Hot Start High-Fidelity DNA polymerase (Genesearch). Reactions were held at 98° C. for 3 min to denature the DNA, followed by 17 cycles of amplification at 98° C. for 10 s, 48° C. for 10 s, and 72° C. for 15 s. Forward-primers, with barcodes 1-62, were designed as specified for the Fusion Method, using a GA spacer and GTGCCAGCMGCCGCGGT as the binding region sequence. A single reverse-primer was used consisting of the reverse adapter, a TC spacer and a binding region sequence of GGACTACHVGGGTVVTCTAA.

Multiplex sequencing of amplicon libraries was performed using an Ion Torrent Personal Genome Machine, utilising the Ion OneTouch™ 2 200 Kit, and Ion PGM™ Sequencing 200 Kit v2 chemistries extended to 535 cycles (Thermo Fisher Scientific).

Sequencing data was analysed with the Ion Torrent Software by mapping against the known 16S V4 sequence for each of the 6 species. To adjust for differences in sequencing depth, the total number of reads was normalized by downsampling to the lowest occurring number of reads.

Confocal Laser Scanning Microscopy

Enamel substrata with attached polymicrobial biofilms were immersed in PBS to rinse away culture media and unattached bacterial cells, prior to immersion in 4% paraformaldehyde, for 30 min fixation at room temperature. They were then immersed in PBS to remove the paraformaldehyde. In preparation for in situ hybridisation, the biofilms were embedded in 20% acrylamide with 0.02% ammonium persulfate and 0.8% N,N,N',N'-tetramethylethylenediamine (TEMED), and subsequently stored in PBS at 4° C.

Polymicrobial biofilms were subjected to fluorescent in situ hybridisation (FISH) using the following customised species-specific probes. The probe sequence ACT CCA GAC TTT CCT GAC labelled with Alexa594 at the 5' detected *S. mutans*, AGA CGC AAT CCC CTC CTT labelled with Alexa405 at the 5' detected *V. dispar*, ACT CTG CCG ACC ATT CTT CT labelled with Alexa647 at the 5' detected *L. casei*, AGA GAT AGA GTT TCT CTT CGG labelled with Alexa488 at the 5' detected *S. sanguis*, CGG TTA TCC AGA AGA AGG GG labelled with Alexa405 at the 5' detected *A. naeslundii*, and CTA ATG GGA CGC AAA GCT CTC labelled with Alexa647 at the 5' detected *F. nucleatum* (Thermofisher, Australia). Biofilms were incubated at 46° C. for 2.5 h, with the hybridisation buffer containing each probe and 10% formamide, as previously described (Zainal-Abidin et al (2012). J Proteome Res. 11(9):4449-4464). Hybridised biofilms were then immersed in a washing buffer (0.45 M NaCl, 20 mM Tris-HCl, 5 mM EDTA, 0.01% SDS) for 25 m at 48° C. and prepared for imaging. Biofilms were visualised on the Zeiss Confocal Laser Scanning Microscope as previously (Zainal-Abidin et al (2012). J Proteome Res. 11(9):4449-4464) and analysed with COMSTAT software to determine biometric parameters.

Scanning Electron Microscopy

Biofilm samples were prepared for scanning electron microscopy analysis as described previously (Zainal-Abidin et al 2012 above; Zhu et al (2013) PLoS One. 8(8):e71727).

Transverse Microradiography

Transverse microradiography was carried out essentially as described previously [Shen et al 2011]. Radiographic images of the lesion and the sound enamel next to it were each scanned six times and averaged to give a demineralized densitometric profile and control sound-enamel densitometric profile and the volume % mineral (vol % min) content profiles were computed. The lesion depth (µm) was determined as the distance to the point at which the mineral content reaches 95% of the sound enamel value. The integrated mineral loss (IML), represented as ΔZd, was calculated by trapezoidal integration as the area between the sound-enamel densitometric profile and that of the demineralized enamel densitometric profile in vol % min·µm.

Biofilm Ion Analyses

Calcium, phosphorous and tin content of polymicrobial biofilm samples were determined by inductively-coupled mass spectrometry essentially as described previously [Dashper et al 2005].

Statistical Analyses

Bacterial species and lesion parameter comparisons. Normality of residuals was checked using Q-Q plots and the Shapiro-Wilk test for normality and homogeneity of variance was tested using Levene's test. As residuals for bacterial species composition did not approximate a normal distribution even following Box-Cox transformation using Minitab version 17 software (Minitab Inc. State College Pa., USA), differences in species proportions were analysed using the Kruskal-Wallis test for more than two independent samples. Post hoc Wilcoxon Rank Sum tests with a Bonferroni correction were used to measure differences between treatments (Sokal and Rohlf (1969). Biometry San Francisco: W.H. Freeman and Co.). For lesion parameter differences, LDs at day 6 were measured on Box-Cox transformed data using a one-way ANOVA with pairwise differences measured using post hoc Tukey tests. Differences in $\Delta Zd$ values at day 6 and both LD and $\Delta Zd$ values at days 12 and 19 were measured using the Kruskal-Wallis test and post hoc Wilcoxon Rank sum tests with a Bonferroni correction. All statistical tests were performed using SPPS version 22 software (IBM SPSS Inc., IL, USA). In all cases, α was set at 0.05.

Results

Development of the Polymicrobial Biofilm Model

Figure 3:
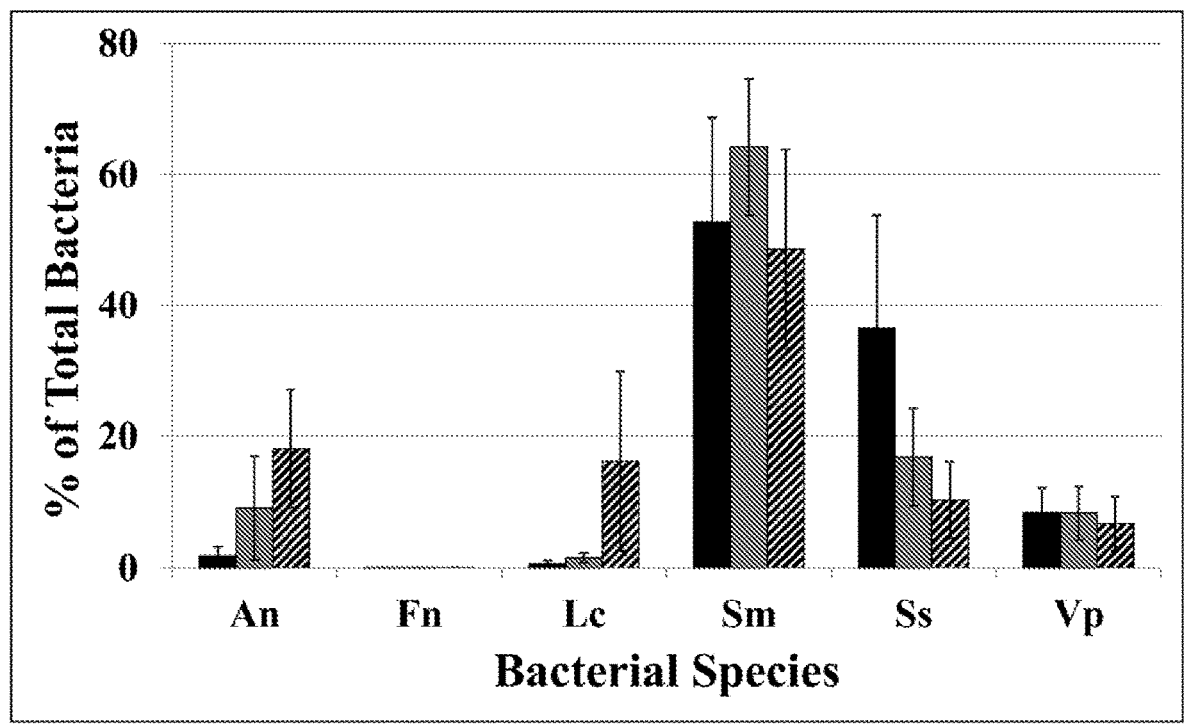
FIG. 3. Average species composition of a six species polymicrobial biofilm cultured with a human enamel substratum in a constant depth film fermenter pulsed four times per day with 1% sucrose. All six species, *A. naeslundii* (An), *F. nucleatum* (Fn), *L. casei* (Lc), *S. mutans* (Sm), *S. sanguinis* (Ss) and *V. parvula* (Vp) were detected at each time point. *S. mutans* remained relatively constant over the 19 days and was the most abundant species. Both *A. naeslundii* and *L. casei* increased in abundance over time whilst *S. sanguinis* decreased. This is consistent with the polymicrobial biofilm becoming more acidic over time. The three bars above each species designation refer to relative abundance on Day 6 (black), Day 12 (grey) and Day 19 (striped) after inoculation.

High numbers of all six bacterial species were present in the polymicrobial inocula as determined by 16s rRNA gene analyses (Table 5). Polymicrobial biofilms established rapidly on the sound human enamel substratum of the constant-depth film fermentor (CDFF) after inoculation when grown in the presence of artificial saliva medium (ASM) with frequent exposures to sucrose. All six bacterial species were detectable in the polymicrobial biofilm of all four biological replicates of the control at every time point, although *F. nucleatum* was never present above 0.01% of the total bacteria present. *A. naeslundii* increased over time from under 2% at day 6 to over 18% of the total bacteria at day 19 (FIG. 3). The proportion of *L. casei* increased dramatically over the course of the experiment and was at an average of 16% of the total bacterial population by day 19. There was a decline in the proportion of *S. sanguinis* from 36% of the total biofilm bacteria on day 6 to less than 11% by day 19. There was no clear trend in the proportions of *S. mutans* over time and it is likely that this species remained relatively stable. *S. mutans* was the most abundant species in the biofilms, accounting for between 48 to 64% of the total bacterial population (FIG. 3).

Figure 4:
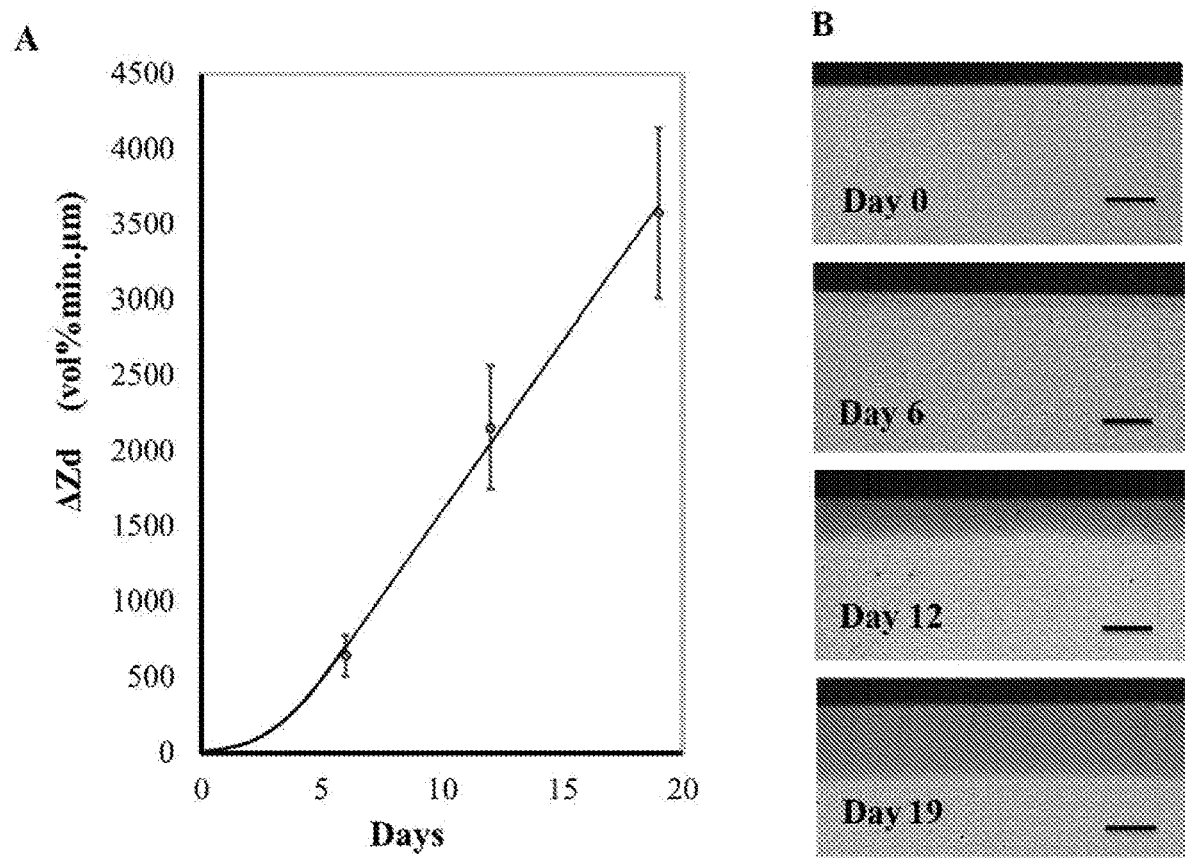
FIG. 4. Enamel subsurface demineralization in the polymicrobial biofilm caries model. A. Integrated mineral loss (vol % min·μm) of the enamel substratum over the 19 day period in the polymicrobial caries model. The data represent four biological replicates of the control (no treatment) and are presented as mean±S.D. B. Representative transverse microradiographs of the enamel substratum showing subsurface demineralization at day 6, 12 and 19. C. Representative electron micrograph of the polymicrobial biofilm from Day 12 showing the intimate association and supragingival plaque like structure of the bacterial biofilm.
Figure 4:
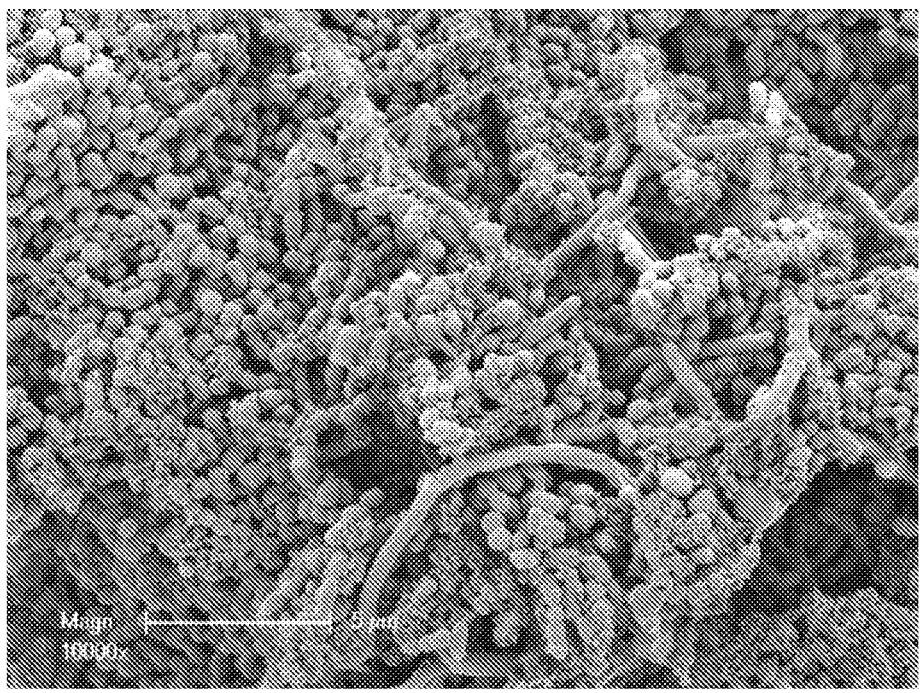

Demineralization of the initially sound human enamel substratum was produced by exposure of the enamel blocks to the sucrose pulsed polymicrobial biofilm. Enamel lesions were generated that maintained an intact surface layer and were similar in that respect to early caries lesions seen in vivo (FIG. 4). The polymicrobial biofilm also had a similar structure to supragingival plaque when imaged by scanning electron microscopy (FIG. 4). Lesion formation progressed in a linear manner after an initial lag period with a mean constant rate of mineral loss from day 6 to day 19 of 225.1 vol % min·µm/day (FIG. 4). There was a mean lesion depth of 87.1±8.4 µm and a mean integrated mineral loss ($\Delta Zd$) of 3575.6±562.0 vol % min·µm on day 19 (Table 6).

TABLE 6

The effect of $SnF_2$, CPP-ACP and CPP-ACP/$SnF_2$ on integrated mineral loss ($\Delta Zd$) and lesion depth (LD) of subsurface lesions formed in the enamel substratum of the polymicrobial biofilm caries model.

| | Day 6 | | Day 12 | | Day 19 | |
|---|---|---|---|---|---|---|
| Group | $\Delta Zd$ (vol % min · µm) | LD (µm) | $\Delta Zd$ (vol % min · µm) | LD (µm) | $\Delta Zd$ (vol % min · µm) | LD (µm) |
| Control | $641.5 \pm 139.0^a$ | $18.0 \pm 3.0^{ab}$ | $2155.2 \pm 407.2^{abc}$ | $49.9 \pm 8.0^{abc}$ | $3575.6 \pm 562.0^{abc}$ | $87.1 \pm 8.4^{abc}$ |
| CPP-ACP | $572.9 \pm 97.80$ | $15.0 \pm 2.1^a$ | $1075.3 \pm 148.0^{ad}$ | $26.3 \pm 4.4^{ade}$ | $2105.4 \pm 346.2^{bd}$ | $52.3 \pm 3.2^{ad}$ |
| $SnF_2$ | $636.7 \pm 129.4$ | $17.6 \pm 1.2^c$ | $1352.1 \pm 147.3^{bde}$ | $37.1 \pm 5.3^{bdf}$ | $2096.3 \pm 66.7^{ae}$ | $46.1 \pm 4.7^{be}$ |
| CPP-ACP + $SnF_2$ | $552.6 \pm 109.2^a$ | $14.3 \pm 2.6^{bc}$ | $1091.3 \pm 138.2^{ce}$ | $28.9 \pm 1.9^{cef}$ | $1395.5 \pm 263.2^{cde}$ | $38.0 \pm 3.4^{cde}$ |

Day 6: same superscripts in LD column indicate significant differences; ($^{ac}p < 0.05$; $^bp < 0.001$): same superscript in $\Delta Zd$ column indicates significant difference ($^ap < 0.05$). All other differences are not significant (p > 0.05).
Day 12: same superscripts in column indicate significant differences. LD - all differences are significantly different (p < 0.05). $\Delta Zd$ - all differences significantly different (p < 0.05) except between CPP-ACP and CPP-ACP + $SnF_2$ (p > 0.05).
Day 19: same superscripts in column indicate significant differences - LD and $\Delta Zd$ - all differences significantly different (p < 0.05) except between $SnF_2$ and CPP-ACP. (p > 0.05).

Effect of $SnF_2$ and CPP-ACP on Composition of the Polymicrobial Biofilm

Figure 5:
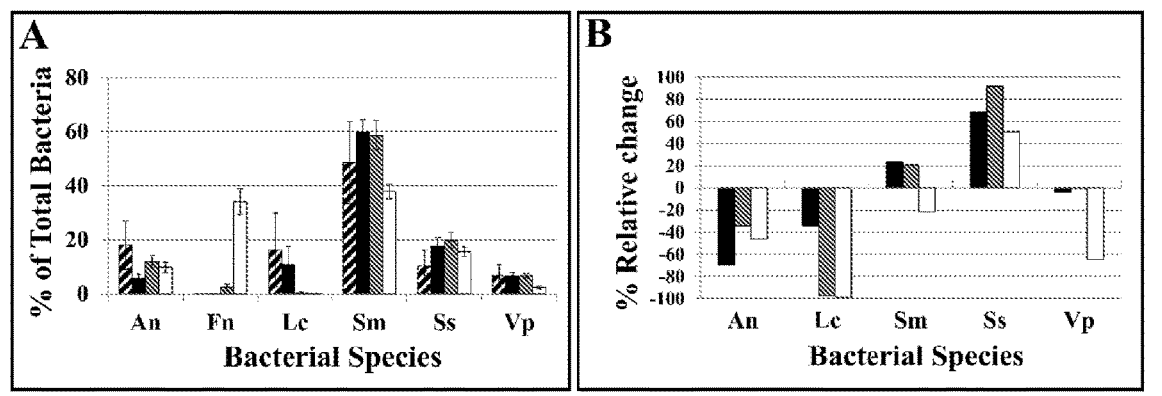
FIG. 5. Effect of twice daily $SnF_2$, 2% CPP-ACP and 2% CPP-ACP-$SnF_2$ addition on the polymicrobial biofilm bacterial species composition in the CDFF on Day 19. A. Bacterial species composition as a percentage of total bacteria in the biofilm (Data and statistical analyses presented in Table 7). B. The change in abundance of each species after treatment relative to the control. *F. nucleatum* is not depicted due to the exceedingly high relative increase in polymicrobial biofilms treated with 2% CPP-ACP-$SnF_2$ of 4,981%. $SnF_2$ treatment had no effect on *F. nucleatum* abundance (−2%) whilst CPP-ACP treatment caused a 355% increase at day 19. Striped bars=control, Black=$SnF_2$, Grey=2% CPP-ACP and White=2% CPP-ACP-$SnF_2$. C. Representative 3D rendered CLSM image of the polymicrobial biofilm treated with CPP-ACP-$SnF_2$ on Day 19. Bacterial cell were stained with four species specific FISH probes (purple—*F. nucleatum*; blue—*A. naeslundii*; red—*S. mutans*; green—*S. sanguinis*).
Figure 5:
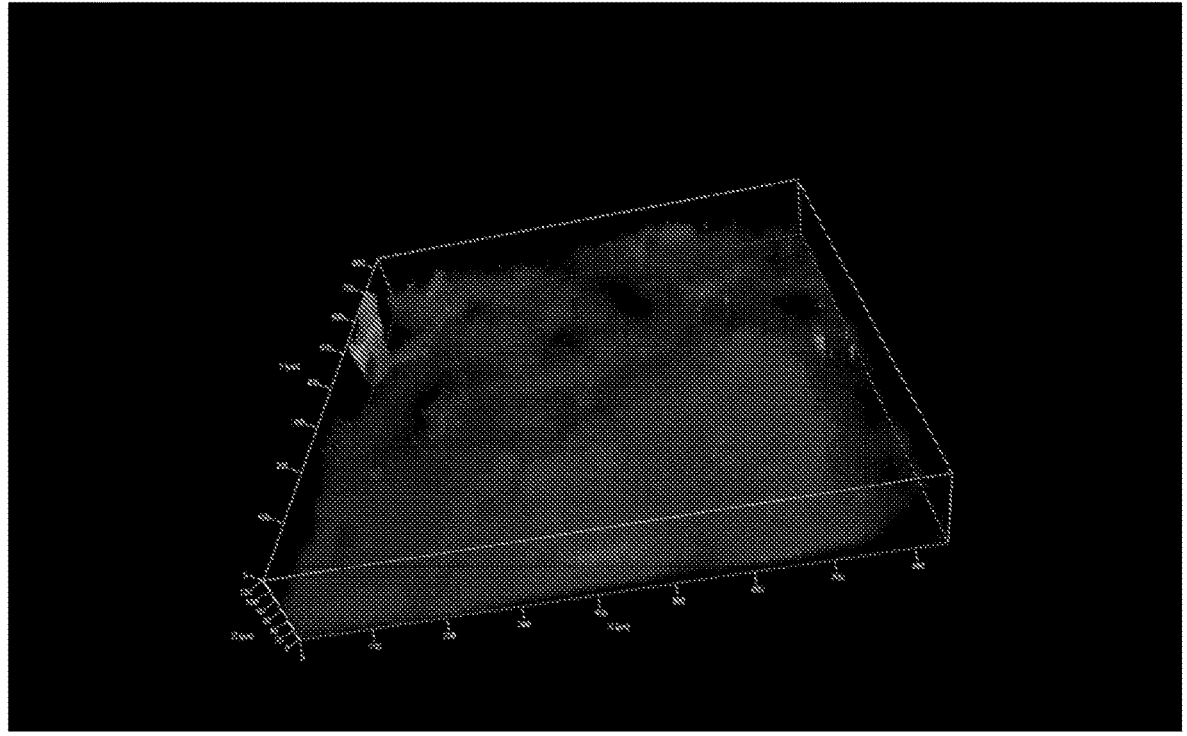

Treatment of the polymicrobial biofilm twice daily with $SnF_2$ significantly reduced the abundance of *A. naeslundii* and increased the abundance of *S. sanguinis* relative to the control at day 19 (FIG. 5, Table 7). Treatment of the polymicrobial biofilm twice daily with CPP-ACP resulted in more significant changes to the composition of the polymicrobial biofilm, especially by day 19 after inoculation. Although *S. mutans* and *V. parvula* proportions remained relatively constant *L. casei* dramatically decreased and *S. sanguinis* and *F. nucleatum* both significantly increased compared with the control (FIG. 5). The largest changes in relative abundance were a consistent >95% decrease in *L. casei* whilst *F. nucleatum* showed the largest mean increase of 355% at day 19 (FIG. 5B, Table 7). The combination of CPP-ACP and $SnF_2$ caused more marked effects on the bacterial composition of the polymicrobial biofilm (FIG. 5 and Table 7). There were notable decreases in the acidogenic and aciduric species, *S. mutans*, *A. naeslundii* and *L. casei*, as well as *V. parvula*. The acid-sensitive species *F. nucleatum* increased dramatically to 34% of the total bacteria becoming the second most abundant species in the polymicrobial biofilm and *S. sanguinis* also increased in abundance by 50%. All six bacterial species were detectable at all times in the treated biofilms. Confocal laser scanning microscopy of the CPP-ACP/$SnF_2$ treated polymicrobial biofilm using specific stains for four of the bacterial species confirmed the emergence of *F. nucleatum* as a major component of the community (FIG. 5).

TABLE 7

Effect of the four treatments on the bacterial species composition as a percentage of total bacteria in the biofilm.

| Treatment | A. naeslundii | F. nucleatum | L. casei | S. mutans | S. sanguinis | V. parvula |
|---|---|---|---|---|---|---|
| Control | $18.11 \pm 8.96^{*a}$ | $0.01 \pm 0.01^{ab}$ | $16.21 \pm 13.64^{ab}$ | $48.56 \pm 15.23$ | $10.37 \pm 5.79^{ab}$ | $6.75 \pm 4.12^{a}$ |
| SnF$_2$/NaF | $5.54 \pm 1.74^{abc}$ | $0.02 \pm 0.01^{cd}$ | $10.67 \pm 6.92^{cd}$ | $59.82 \pm 4.59^{a}$ | $17.47 \pm 3.44^{a}$ | $6.50 \pm 1.48^{b}$ |
| CPP-ACP | $11.93 \pm 2.34^{b}$ | $2.43 \pm 1.21^{ace}$ | $0.38 \pm 0.23^{ac}$ | $58.70 \pm 5.47^{b}$ | $19.85 \pm 2.86^{bc}$ | $6.71 \pm 0.89^{c}$ |
| CPP-ACP + SnF$_2$/NaF | $9.76 \pm 2.01^{c}$ | $34.13 \pm 4.88^{bcde}$ | $0.18 \pm 0.07^{bd}$ | $37.95 \pm 2.64^{ab}$ | $15.61 \pm 1.76^{c}$ | $2.37 \pm 0.45^{abc}$ |
| Overall p-value | <0.001 | <0.001 | <0.001 | 0.004 | <0.001 | 0.019 |

*Mean ± standard deviation. Proportion of bacterial species in polymicrobial biofilm exposed to four treatments at 19 days.
$^{abcde}$Same superscripts in column indicate significant differences (p < 0.05). n = 5-21.

All comparisons across treatments performed with a Kruskal-Wallis test (see overall p-value) and pairwise differences between treatments were measured with post hoc Wilcoxon Ranked Sum tests with a Bonferroni correction.

Effect of SnF$_2$ and CPP-ACP Preparation on Enamel Demineralization

Treatment of the polymicrobial biofilm with SnF$_2$ resulted in a significant 50.2% reduction in rate of demineralization to 112.1 vol % min·μm/day between day 6 and day 19 (Table 6). This reduction was not statistically different to that seen with the CPP-ACP treatment which also produced a 50.2% reduction in demineralization rate (112.1 vol % min·μm/day) over the same period. However the reduction in demineralization rate to 64.1 vol % min·μm/day was significantly greater (72%) for the combined SnF$_2$/CPP-ACP treatment (Table 6). ICP-MS analysis of the biofilms demonstrated a four-fold increase in calcium and a three-fold increase in phosphorous when CPP-ACP was used with SnF$_2$. Interestingly SnF$_2$ treatment resulted in a two-fold increase in both calcium and phosphorous relative to the control. Stannous concentration peaked at 1.0 nmol/mg biofilm wet weight during both the SnF$_2$ preparation and CPP-ACP-SnF$_2$ treatments. However this concentration was reached earlier with the CPP-ACP-SnF$_2$ treatment.

Discussion

The six species bacterial biofilm communities produced in the CDFF with four pulses of sucrose per day were dominated by the more acidogenic and aciduric, and therefore cariogenic, species S. mutans, A. naeslundii and L. casei which together constituted 85% of the polymicrobial biofilm on day 19. This proportion had increased from 55% on day 6. When examining just the proportions of A. naeslundii and L. casei in the control biofilm there was an increase from 2.5% of total bacterial cells to 34% from day 6 to day 19 (FIG. 3). This indicates a highly acidic and cariogenic environment, which is consistent with the low levels of the neutrophilic species F. nucleatum and the rapid, constant and reproducible rate of demineralization in this model (FIG. 4).

Having established the reproducibility of the model the effects of twice daily additions were studied of 290 ppm fluoride as a mixture of SnF$_2$ (220 ppm F):NaF (70 ppm F), which was selected to represent a five-fold dilution in saliva of current 1450 ppm F dentifrices using SnF$_2$/NaF. In the study A. naeslundii was significantly reduced and S. sanguinis significantly increased in relative abundance in the polymicrobial biofilm during SnF$_2$ treatment. Sn accumulated in the polymicrobial biofilms up to a concentration of 119 ppm. SnF$_2$ reduced the rate of enamel demineralization in this study by 50% over 19 days of twice daily exposure and the major mechanism is likely to be related to the action of the F ion promoting remineralization.

CPP-ACP addition not only resulted in a significant 50% reduction in demineralization rate, it also suppressed the emergence of the highly acidogenic L. casei. In addition there were reproducible increases in the abundance of the acid-sensitive and beneficial symbionts F. nucleatum and S. sanguinis (FIG. 5, Table 7). This indicates that CPP-ACP had a prebiotic effect on biofilm development in this model.

An enhanced prebiotic effect on the bacterial composition of the polymicrobial biofilm by CPP-ACP and SnF$_2$ was noted with all three acidogenic and aciduric species decreasing in abundance. V. parvula also decreased which may indicate a decrease of lactate due to the inhibition of glycolysis and F. nucleatum became a major component of the biofilm. These changes were associated with the highly significant 72% inhibition of enamel demineralization rate which would translate to a significant improvement in oral health. The additive effect of the SnF$_2$ and CPP-ACP in promoting prebiosis was attributed to the ability of the stannous ions (Sn$^{2+}$) to cross-link the CPP-ACP and better deliver the prebiotic to the polymicrobial biofilm and the intra-oral/tooth surface as demonstrated in Example 3.

It will be understood that the invention disclosed and defined in this specification extends to all alternative combinations of two or more of the individual features mentioned or evident from the text or drawings. All of these different combinations constitute various alternative aspects of the invention.

The invention claimed is:

1. A method of treating periodontitis in an individual in need thereof having at least moderate periodontitis, the method comprising administering one or both of stabilized amorphous calcium phosphate (ACP) and stabilized amorphous calcium fluoride phosphate (ACFP) to the oral cavity of the individual, thereby treating periodontitis, wherein the stabilized ACP is not a stannous-associated phosphopeptide (PP) stabilized amorphous calcium phosphate (ACP) and the stabilized ACFP is not a stannous-associated phosphopeptide (PP) stabilized amorphous calcium fluoride phosphate (ACFP).

2. The method according to claim 1, wherein the method further comprises, prior to the administering, an initial step of identifying the individual as having at least moderate periodontitis.

3. The method according to claim 1, wherein the method further comprises, prior to the administering, performing a dental procedure on the individual.

4. The method according to claim 3, wherein the dental procedure is selected from debridement, scaling, root planing, and any other procedure to remove subgingival or supragingival bacteria.

5. The method according to claim 1, wherein the stabilized amorphous calcium phosphate (ACP) is phosphopeptide stabilized and the stabilized amorphous calcium fluoride phosphate (ACFP) is phosphopeptide stabilized.

6. The method according to claim 5, wherein the phosphopeptide is a casein phosphopeptide.

7. The method according to claim 1, wherein the method comprises administering the stabilized amorphous calcium phosphate (ACP) and/or stabilized amorphous calcium fluoride phosphate (ACFP) in any one of the following types of compositions:

toothpastes, toothpowders, liquid dentifrices, mouthwashes, mouthrinses, mouth sprays, varnish, dental cement, troches, chewing gums, dental pastes, gingival massage creams, gargle tablets, dairy products and other foodstuffs.

8. The method according to claim 7, wherein the composition is a chewing gum.

9. The method according to claim 8, wherein the chewing gum contains and amount of ACP or ACFP selected from about 15 mg, 20 mg, 25 mg, 30 mg, 35 mg, 40 mg, 45 mg, 50 mg, 55 mg and 60 mg.

10. The method according to claim 9, wherein the chewing gum contains about 18.8 or about 56.4 mg of stabilized ACP or ACFP.

11. The method according to claim 1, wherein the individual in need thereof has moderate periodontitis.

12. The method according to claim 1, wherein the individual in need thereof has severe periodontitis.

* * * * *